United States Patent
Tuffin et al.

(10) Patent No.: US 6,696,110 B1
(45) Date of Patent: Feb. 24, 2004

(54) LIQUID CRYSTALLINE ALKENYL COMPOUNDS INCORPORATING AN HETEROCYCLIC FIVE-MEMBERED RING

(75) Inventors: Rachel P Tuffin, Malvern (GB); Steven M Kelly, Hull (GB); Neil L Campbell, Hull (GB); Warren L Duffy, Hull (GB); Janine H Wild, Hull (GB)

(73) Assignee: Qinetiq Limited, Farnborough (GB)

( * ) Notice: Subject to any disclaimer, the term of this patent is extended or adjusted under 35 U.S.C. 154(b) by 0 days.

(21) Appl. No.: 09/958,154

(22) PCT Filed: Mar. 29, 2000

(86) PCT No.: PCT/GB00/01203

§ 371 (c)(1),
(2), (4) Date: Nov. 26, 2001

(87) PCT Pub. No.: WO00/60027

PCT Pub. Date: Oct. 12, 2000

(30) Foreign Application Priority Data

Apr. 6, 1999 (GB) .............................................. 9907645

(51) Int. Cl.[7] ...................... C09K 19/34; C07D 333/16; C07D 285/12; C07D 277/24; C07D 307/34; C07D 233/38
(52) U.S. Cl. .................... 428/1.1; 252/299.61; 548/136; 548/143; 548/146; 548/215; 549/29; 549/49; 349/136
(58) Field of Search ...................... 428/1.1; 252/299.61, 252/299.62, 299.63, 299.64, 299.67; 548/136, 143, 146, 215; 549/29, 429; 349/134, 136

(56) References Cited

U.S. PATENT DOCUMENTS 6,224,787 B1 * 5/2001 Hanna et al. ............. 252/299.3

FOREIGN PATENT DOCUMENTS

| EP | 0 476 567 A1 | 3/1993 |
|---|---|---|
| EP | 0 563 768 A | 10/1993 |
| EP | 0 735 125 A2 | 3/1995 |
| EP | 0 735 125 A3 | 3/1995 |
| EP | 0 864 631 | 9/1998 |
| WO | WO 98/13325 | 4/1998 |

* cited by examiner

Primary Examiner—Shean C Wu
(74) Attorney, Agent, or Firm—Nixon & Vanderhye P.C.

(57) ABSTRACT

Liquid crystal mixtures comprising at least one of the compounds of formula (I) containing a heterocyclic five-membered ring and with a carbon-carbon double bond in the termninal group are new.

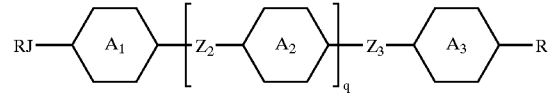

(I)

$RJ=C_nH_{2n+1}CH=CHC_mH_{2m}Z_1$; $n=1-5$; $m=0-5$; and $q=0$, 1 or 2; A1 and A2=2,5-disubstituted furan, 2,5-disubstituted thiophene, 2,5-disubstituted oxazole, 2,5-disubstituted thiazole, 2,5-disubstituted 1,3,4-oxadiazole, 2,5-disubstituted 1,3,4-thiadiazole, 1,4-disubstituted benzene, 2,5-disubstituted pyrimidine, 2,5-disubstituted pyridine, 2,6-disubstituted naphthalene; laterally substituted 1,4-disubstituted benzene, laterally substituted 2,5-disubstituted pyrimidine, laterally substituted 2,5-disubstituted pyridine or laterally substituted 2,6-disubstituted naphthalene (lateral substituents=F, Cl, Br or CN); A3=any A1 or 1,4-disubstituted bicyclo(2.2.2)octane, trans-1,4-disubstituted cyclohexane, trans-2,5-disubstituted dioxane or 1,4-disubstituted piperidine; Z1=O, COO or OOC; Z2 and Z3=direct bond, COO, OOC, C2H4, CH2O, OCH2, C4H8, C3H6O, (E)-CH=CHC2H4, (Z)-CH2CH=CHCH2, (E)-CH=CHCH2O or —C equivalent to C—; R=1–20C alkyl, alkoxy, alkenyl, alkenyloxy, alkanoyloxy, alkenoyloxy or $OC_pF_{2p+1}$; and $p=1-20$. When Z1=O and m=1, 3 or 5 the carbon-carbon double bond configuration in RJ is E. When Z1=O and m=2 or 4 the carbon-carbon double bond configuration in RJ is Z. When Z1=COO or OOC and m=0, 2 or 4 the carbon-carbon double bond configuration in RJ is E. When Z1=COO or OOC and m=1, 3 or 5 the carbon-carbon double bond configuration in RJ is Z.

10 Claims, 1 Drawing Sheet

LIQUID CRYSTALLINE ALKENYL COMPOUNDS INCORPORATING AN HETEROCYCLIC FIVE-MEMBERED RING

The present invention describes new compounds. In particular it describes compounds for use in liquid crystal mixtures and in liquid crystal displays (LCDs) or in applications relating to inter alia thermography utilising nematic liquid crystal or chiral nematic liquid crystal mixtures.

LCDs, such as multiplexed Twisted Nematic TN-LCDs, Super Twisted Nematic STN-LCDs, Super Birefringent SBE-LCDs, Electrically Controlled Birefringence ECB-LCDs, or flexoelectric LCDs are currently used or being developed for computer monitors, laptop or notebook computers, portable telephones, video telephones, personal digital assistants, etc. The optical, electrical and temporal performance, e.g., contrast, threshold and driving voltages, and response times, of such displays depends crucially on the ratios of the elastic constants ($k_{33}$, $k_{22}$, $k_{11}$) and the cell gap, d. In addition, flexoelectric LCDs also require nematic mixtures with advantageous ratios of the flexoelectric coefficients. Large banana shaped molecules have been found to increase the flexoelectric coefficients of nematic mixtures (1998, P57, Proceedings Freiburger Arbeitstagung Fl üssigkristalle, Freiburg, Germany). However, due to their strongly non-linear shape and large number of aromatic rings and conjugated linking groups, they are highly viscous and relatively insoluble. They also exhibit high melting points and unusual smectic phases, which limits their miscibility with the nematic phase. Currently commercially available nematic mixtures for sophisticated high-information-content LCDs, such as STN-LCDs, incorporate trans-1,4-disubstituted-cyclohexyl derivatives with a terminal alkenyl chain (i.e., incorporating a carbon-carbon double bond) directly attached to the cyclohexane ring in order to produce the necessary elastic constant ratios for short response times, high multiplexing rates and low driving voltages. Such materials are costly and difficult to synthesise due to the requirement for a trans configuration of the 1,4-disubstituted cyclohexane ring and the necessity of synthesising the carbon-carbon double bond stepwise from this trans-1,4-disubstituted-cyclohexyl intermediate. If the carbon-carbon double bond is substituted at both carbon atoms, it must have a trans (E) configuration in order to exhibit an advantageous combination of elastic constants and to have an acceptably high nematic-isotropic transition temperature (N-I). The trans configuration is then generally produced by isomerisation of the cis (Z) form generated by the preceding Wittig reaction. These materials exhibit low or intermediate values of birefringence ($\Delta n$) due to the presence of the saturated cyclohexane rings. As the ratio d. $\Delta n$ determines the optical properties of TN-LCDs and is fixed for driving the LCD in the first or second minimum, it is clear that higher values of $\Delta n$ would allow smaller cell gaps. As the response time, $t_{on}$ of TN-LCDs is inversely proportional to $d^2$, smaller cell gaps have a dramatic effect on $t_{on}$. Low values of $t_{on}$ also allow the use of colour or more shades of colour due to the shorter frame times. Since the response times $t_{on}$ and especially $t_{off}$ also strongly depend on the magnitude of the viscosity of the nematic mixture, the combination of a low viscosity and a high birefringence would be highly advantageous. Furthermore TN-LCDs using thin film transistors (TFTs) as the backplate for active addressing require nematic liquid crystal mixtures with a positive dielectric anisotropy ($\Delta \epsilon$) and a very high resistivity (holding ratio $\geq 98\%$) in order to avoid dielectric breakdown and inferior display performance. It has been shown that standard nematic liquid crystals with a terminal cyano group are unsuitable for TN-TFT-LCDs since they lead to low resistivity values due in part to their ability to solvate ions present in the alignment layers and electrodes. This has led to the wide-spread use of 'super-fluorinated' nematic liquid crystals with terminal trifluoromethoxy (DE 3732284 A1), difluoromethyl (WO 90/01056) or fluorine endgroups (JP2-233626, EPA 0 568 040 A1, EPA 0 563 981 A2) and/or several lateral fluoro substituents. However, this leads in general to low nematic-isotropic transition temperatures (N-I) for two-ring compounds. This requires a disproportionate use of three-ring compounds resulting in a high viscosity for the nematic mixture. There is therefore a requirement for synthetically readily-accessible nematic liquid crystals of high birefringence, low viscosity advantageous ratios of elastic constants and flexoelectric coefficients, as well as a relatively high value of N-I and a low melting point.

Liquid crystals with a five-membered heterocyclic ring are known (DE 3346175; EP 0 461 620) and are reviewed in for example Wiss. Z. Univ. HalleXXIX'80 M, H. 3, pp 35–55. They are generally characterised by a strong tendency for smectic phase formation (Mol. Cryst. Liq. Cryst., (1990), Vol.191, pp 223). Two-ring alkyl benzoates incorporating a five-membered heterocyclic ring, such as 2,5-disubstituted furan or 2,5-disubstituted 1,3,4-thiadiazole, are known (EP 0 461 620; Mol. Cryst. Liq. Cryst., (1990), Vol. 191, pp 223). However, they are either non mesomorphic or exhibit smectic phases. Liquid crystals with a carbon-carbon double bond are also known (U.S. Pat. No. 4,676,604; U.S. Pat. No. 4,621,901; EPA 0195974; EPA 0315014; EPA 0355552) and are reviewed in for example Liq. Cryst., (1996) Vol. 20, pp 493. No alkenyl compounds incorporating a five-membered heterocyclic ring are described.

For all the above applications it is not usual for a single compound to exhibit all of the properties highlighted, normally mixtures of compounds are used which when mixed together induce the desired phases and required properties.

The present invention seeks to overcome or alleviate some of the above problems by incorporating a 5-membered heterocyclic ring in the core of a liquid crystal molecule in combination with a carbon-carbon double bond in the terminal end group of the molecule.

According to this invention compounds are provided of Formula I:

Formula I wherein

RJ is $C_nH_{2n+1}CH=CHC_mH_{2m}Z_1$ n may be 1–5;

m may be 0–5;

q may be 0, 1 or 2;

$A_1$, $A_2$, are independently chosen from 2,5-disubstituted furan, 2,5-disubstituted thiophene, 2,5-disubstituted oxazole, 2,5-disubstituted thiazole, 2,5-disubstituted 1,3,4-oxadiazole, 2,5-disubstituted 1,3,4-thiadiazole, 1,4-disubstituted benzene, 2,5-disubstituted pyrimidine, 2,5-disubstituted pyridine, 2,6-disubstituted naphthalene;

laterally substituted 1,4-disubstituted benzene, laterally substituted 2,5-disubstituted pyrimidine, laterally substituted 2,5-disubstituted pyridine, laterally substituted 2,6-disubstituted naphthalene wherein the lateral substituents are independently selected from F, Cl, Br or CN and may be present in any of the available substitution positions;

$A_3$ may be 2,5-disubstituted furan, 2,5-disubstituted thiophene, 2,5-disubstituted oxazole, 2,5-disubstituted thiazole, 2,5-disubstituted 1,3,4-oxadiazole, 2,5-disubstituted 1,3,4-thiadiazole, 1,4-disubstituted benzene, 2,5-disubstituted pyrimidine, 2,5-disubstituted pyridine, 2,6-disubstituted naphthalene; laterally substituted 1,4-disubstituted benzene, laterally substituted 2,5-disubstituted pyrimidine, laterally substituted 2,5-disubstituted pyridine, laterally substituted 2,6-disubstituted naphthalene wherein the lateral substituents are independently selected from F, Cl, Br or CN and may be present in any of the available substitution positions;

1,4-disubstituted bicyclo(2.2.2)octane, trans-1,4-disubstituted cyclohexane, trans-2,5-disubstituted dioxane, 1,4-disubstituted piperidine, $Z_1$ may be O, COO, OOC;

$Z_2$, $Z_3$ are independently chosen from a direct bond, COO, OOC, $C_2H_4$, $CH_2O$, $OCH_2$, $C_4H_8$, $C_3H_6O$, (E)-CH=CHC$_2$H$_4$, (Z)-CH$_2$CH=CHCH$_2$, (E)-CH=CHCH$_2$O, —C≡C— R may be alkyl, alkoxy, alkenyl, alkenyloxy, alkanoyloxy, alkenoyloxy or $OC_pF_{2p+1}$, R may contain 1 to 20 carbon atoms and may be branched or a straight chain;

p is 1–20;

provided that:

when $Z_1$ is O and m is 1, 3 or 5 the carbon-carbon double bond configuration in RJ is E and when $Z_1$ is O and m is 2 or 4 the carbon-carbon double bond configuration in RJ is Z and when $Z_1$ is COO or OOC and m is 0, 2 or 4 the carbon-carbon double bond configuration in RJ is E and when $Z_1$ is COO or OOC and m is 1, 3 or 5 the carbon-carbon double bond configuration in RJ is Z.

The structural and other preferences are expressed below on the basis of inter alia desirable liquid crystalline characteristics, in particular an advantageous combination of dielectric constants and high resistivity in the nematic phase, a high nematic-isotropic liquid transition temperature and ready synthesis from commercially available starting materials, some of which may already incorporate at least one carbon-carbon double bond with the desired configuration and position.

Preferably n is 1–3;

Preferably m is 0–3;

Preferably n+m is ≦6;

Preferably p is 3–7;

Preferably q is 0 or 1 and when q is 0 then both $A_1$ and $A_3$ are aromatic;

Preferably $A_1$ is a five-membered heterocyclic ring;

Preferably $A_2$ is 1,4-disubstituted benzene;

Preferably $Z_1$ is O or COO;

Preferably $Z_2$ and $Z_3$ are direct bonds.

Overall preferred structures for formula I are those listed below:

Preferably q is 0 or 1 and when q is 0 then $A_3$ is aromatic;

Preferably $A_1$, $A_2$, are 2,5-disubstituted furan, 2,5-disubstituted thiophene, 2,5-disubstituted; oxazole, 2,5-disubstituted thiazole, 2,5-disubstituted 1,3,4-oxadiazole, 2,5-disubstituted; 1,3,4-thiadiazole, 1,4-disubstituted benzene;

Preferably $Z_1$ is O, COO;

Preferably $Z_2$, $Z_3$ are direct bonds or —C≡C—

Preferably R is alkyl, alkoxy, alkenyl or alkenyloxy and has one to seven carbon atoms.

Especially preferred structures for formula I are those listed below:

wherein R is alkyl, alkoxy, alkenyl or alkenyloxy and contains 1–7 carbon atoms.

According to a further aspect of this invention a liquid crystal mixture comprises at least one of the compounds of Formula I.

According to a further aspect of this invention a device comprises two spaced walls each bearing electrode structures and treated on at least one facing surface with an alignment layer, a layer of a liquid crystal material enclosed between the cell walls, characterised in that it comprises a compound of Formula I.

The device includes both passive and active devices and may be Twisted Nematic (TN) or a Super Twisted Nematic (STN) Device.

According to a further aspect of this invention a bistable nematic liquid crystal device comprises;

two cell walls enclosing a layer of liquid crystal material;

electrode structures on both walls;

a surface alignment on the facing surfaces of both cell walls providing alignment to liquid crystal molecules;

means for distinguishing between switched states of the liquid crystal material;

a surface alignment grating on at least one cell wall that permits the liquid crystal molecules to adopt two different pretilt angles in the same azimuthal plane;

the arrangement being such that two stable liquid crystal molecular configurations can exist after suitable electrical signals have been applied to the electrodes;

wherein the layer of liquid crystal material comprises a material of Formula I.

The grating may have a symmetric or an asymmetric groove profile.

The grating may have an asymmetric groove profile which will induce a pretilt of less than 90°, e.g. 50° to 90°. An asymmetric profile may be defined as a surface for which there does not exist a value of h such that;

$$\Psi_x(h-x)=\Psi_x(h+x) \tag{1}$$

for all values of x, where $\Psi$ is the function describing the surface.

The gratings may be applied to both cell walls and may be the same or different shape on each wall. Furthermore the grating profile may vary within each pixel area, and or in the inter pixel gaps between electrodes. One or both cell walls may be coated with a surfactant such as lethecin.

The liquid crystal material may be non twisted in one or both stable molecular configurations.

The cell walls may be formed of a relatively thick non flexible material such as a glass, or one or both cells walls may be formed of a flexible material such as a thin layer of glass or a flexible plastic material e.g. polyolefin or polypropylene. A plastic cell wall may be embossed on its inner surface to provide a grating. Additionally, the embossing may provide small pillars (e.g. of 1–3 $\mu$m height and 5–50 $\mu$m or more width) for assisting in correct spacing apart of the cell walls and also for a barrier to liquid crystal material flow when the cell is flexed. Alternatively the pillars may be formed by the material of the alignment layers.

The grating may be a profiled layer of a photopolymer formed by a photolithographic process e.g. M C Hutley, Diffraction Gratings (Academic Press, London 1982) p 95–125; and F Horn, Physics World, 33 (March 1993). Alternatively, the bigrating may be formed by embossing; M T Gale, J Kane and K Knop, J App. Photo Eng, 4, 2, 41 (1978), or ruling; E G Loewen and R S Wiley, Proc SPIE, 88 (1987), or by transfer from a carrier layer.

The electrodes may be formed as a series of row and column electrodes and an x,y matrix of addressable elements or display pixels. Typically the electrodes are 200 $\mu$m wide spaced 20 $\mu$m apart.

Alternatively, the electrodes may be arranged in other display formats e.g. r-θ matrix or 7 or 8 bar displays.

The materials of the present invention may also be used in devices which make use of in-plane switching and this means that there may be electrodes on one or two of the substrates Compounds of formula I can be prepared by various routes. Typically the aromatic heterocyclics can be prepared by the Suzuki aryl-aryl cross-coupling reaction (Chem. Rev., (1995) Vol. 95, pp 2457) of a aromatic boronic acid with an aromatic halide in the presence of a base such as aqueous sodium carbonate solution, a catalyst, such as tetrakis (triphenylphosphine)palladium(0), and a suitable solvent, such as tetrahydrofuran or 1,2-dimethoxyethane. Alternatively they can be synthesised by the Stille coupling of aryl stannanes with aryl halides in the presence of a catalyst, such as tetrakis(triphenylphosphine)palladium(0), and a suitable solvent, such as N,N-dimethylformamide or 1,2-dimethoxyethane (Angew. Chem., (1986) Vol. 98, pp 504). An alternative approach is the use of ring closure reactions. For example 2,5-disubstituted furan and 2,5-disubstituted thiophene derivatives can be prepared by treatment of a 1,4-disubstituted butanedione with phosphorous oxychloride or phosphorous pentasulphide, respectively, in a suitable solvent, such as pyridine (Z. Chem., (1975) Vol. 15, pp 222). 2,5-Disubstituted oxazole and 2,5-disubstituted thiazole derivatives can be prepared by treatment of suitable N-benzoyl-ω-amino-acetophenone derivatives, formed in a one-pot-reaction from the corresponding 4-alkoxy-ω-amino-acetophenone-hydrochlorides and 4-substituted-benzoylchlorides, with phosphorous oxychloride or phosphorous pentasulphide, respectively, in a suitable solvent, such pyridine (J. prakt. Chem., (1979) Vol. 321, pp 643). 2,5-Disubstituted-1,3,4-oxadiazole and 2,5-disubstituted-1,3,4-thiadiazole derivatives can be prepared by treatment of a bishydrazide derivative with phosphorous oxychloride or phosphorous pentasulphide, respectively, in a suitable solvent, such as pyridine (J. Amer. Chem. Soc., (1955) Vol. 77, pp 1850; J. prakt. Chem., (1980) Vol. 322, pp 933). Typically the ethers can be prepared by the Mitsunobu reaction (Synthesis, (1981) pp 1) of a phenol with an alcohol or alkenol in the presence of triphenyl phosphine, a dehydrating agent, such as diethyl azodicarboxylate, and a suitable solvent, such as tetrahydrofuran or N,N'-dimethyiformamide. Alternatively they can be synthesised by alkylation of a secondary alcohol with alkyl or alkenyl bromide or the tosylate of the appropriate alcohol or alkenol in the presence of a suitable base, such as potassium tert.-butoxide, and a suitable solvent, such as tert.-butylmethyl ether or 1,2-dimethoxyethane (J. Mater. Chem., (1994) Vol. 4, pp 1673). Alternatively they can be synthesised by alkylation of a phenol with an alkyl or alkenyl bromide or the tosylate of the appropriate alcohol or alkenol in the presence of a suitable base, such as potassium carbonate, and a suitable solvent, such as ethyl methyl ketone or cyclohexanone in a Williamson ether synthesis. 1,2-Disubstituted acetylenes and tolanes can be prepared by metal catalysed cross-coupling reactions of mono-substituted acetylenes with aryl and cyclohexyl halides or triflates in the presence of an appropriate base such as triethylamine and appropriate metal based catalysts such as tetrakis(triphenylphosphine)palladium(0) and copper(I) iodide or palladium(II) acetate and triorthotoluylphosphine ligands (Mol. Cryst. Liq. Cryst., (1990) Vol. 148, pp 193; Mol. Cryst. Liq. Cryst., (1995) Vol. 260, pp 93). The esters can be prepared by esterification (Angewandte Chemie (1978) Vol. 90, pp 556) of the appropriate phenol or secondary alcohol with an alkanoic acid or alkenoic acid in the presence of 4-(dimethylamino)pyridine, a dehydrating agent, such as N,N'-dicyclohexyicarbodiiimide, and a suitable solvent, such as dichloromethane or N,N'-dimethylformamide. Alternatively they can be synthesised by esterification of the appropriate phenol or secondary alcohol with an alkanoic or alkenoic acid chloride (produced, for example, from the corresponding alkanoic or alkenoic acid by the action of thionyl chloride or oxalyl chloride) in the presence of a base, such as pyridine or tnethylamine, and a suitable solvent, such as toluene or dichloromethane.

The invention will now be described, by way of example only, with reference to the following examples and diagrams:

DETAILED DESCRIPTION OF PREFERRED EMBODIMENT

In the following examples K refers to the crystalline state, N the nematic phase, SmA a smectic A phase, SmB a smectic B phase, SmC a smectic C phase and SmX an undefined liquid crystal smectic phase. Values contained in brackets [ ] are nematic-isotropic transition temperatures extrapolated from mixtures of individual compounds and the commercially available (Merck, Darmstadt) nematic mixture ZLI 3086.

EXAMPLE 1

Preparation of 2-(4-[(E)-hex-2-Enoyloxy]phenyl)-5-pentylthiophene

Dicyclohexylcarbodiimide (0.2 g) was added to a solution of 2-(4-hydroxyphenyl)-5-pentylthiophene (0.25 g), (E)-hex-2-enoic acid, (0.1 g) 4-(dimethyiamino)pyridine (0.05 g) and dichloromethane (20 cm$^3$) at 0° C. under an atmosphere of nitrogen. The reaction mixture was stirred overnight at room temperature, filtered to remove inorganic material and the filtrate evaporated down. The residue was purified by column chromatography on silica gel using hexane/ethyl acetate (9/1 v/v) as eluent and recrystallisation from hexane to yield 0.17 g of 2-(4-[(E)-hex-2-enoyloxy] phenyl)-5-pentylthiophene, K 47° C., [N 46° C.], I.

The 2-(4-hydroxyphenyl)-5-pentylthiophene required as starting material could be prepared as follows:

A solution of 2-pentylthiophene, (25.2 g) N-bromosuccinimide (25.5 g) and a 1:1 chloroform acetic acid mixture (100 cm$^3$) was heated under reflux for 1 h. Water (10 cm$^3$) was added and the resultant solution stirred for 10 min under an atmosphere of nitrogen. The organic layer was separated off and the aqueous layer extracted with diethyl ether (2×50 cm$^3$). The combined organic layers were washed with brine (2×100 cm$^3$), dried (MgSO$_4$), filtered and then evaporated down. The residue was purified by distillation (Bp 132–134° C. at 15–20 mm Hg.) to yield 32.6 g of 2-bromo-5-pentylthiophene.

A solution of 2-bromo-5-pentylthiophene (10.0 g), 4-methoxyphenyl boronic acid (7.9 g), 2M aqueous sodium carbonate solution (150 cm$^3$), 2.3 g tetrakis (triphenylphosphine)palladium (0) and dimethoxyethane (100 cm$^3$) was heated under reflux for 6 h. 20% Hydrochloric acid (200 cm$^3$) was added to the cooled reaction mixture and the resultant mixture extracted with diethyl ether (5×100 cm$^3$). The combined organic layers were washed with 20% hydrochloric acid (1×100 cm$^3$), brine (2×100 cm$^3$) and then dried (MgSO$_4$), filtered and evaporated down. The residue was purified by column chromatography on silica gel using a 4:1 hexane/dichloromethane mixture as eluent and recrystallisation from ethanol to yield 8.7 g of 2-(4-methoxyphenyl)-5-pentylthiophene, K 58–60° C., I.

A solution of boron tribromide (3.2 cm$^3$) and dichloromethane (30 cm$^3$) was added dropwise to a solution of 2-(4-methoxyphenyl)-5-pentylthiophene (10.0 g) and dichloromethane (70 cm$^3$) at 0° C. under an atmosphere of nitrogen. The reaction solution was stirred overnight at room temperature and water (100 cm$^3$) added. The organic layer was separated off and the aqueous layer extracted with dichloromethane (2×100 cm$^3$). The combined organic layers were washed with brine (2×100 cm$^3$) and then dried (MgSO$_4$), filtered and evaporated down. The residue was purified by column chromatography on silica gel using a 4:1 hexane/dichloromethane mixture as eluent and recrystallisation from hexane to yield 7.7 g of g 2-(4-hydroxyphenyl)-5-pentylthiophene, K 100–102° C., I.

The following compounds could be obtained analogously:

2-(4-[(E)-But-2-enoyloxy]phenyl)-5-propylthiophene, K, 37° C., N 47° C., I.

2-(4-[(E)-Pent-2-enoyloxy]phenyl)-5-propylthiophene, K, 32° C., [N 17° C.], I.

2-(4-[(E)-Hex-2-enoyloxy]phenyl)-5-propylthiophene, K, 16° C., N 42° C., I.

2-(4-[(Z)-Hex-3-enoyloxy]phenyl)-5-propylthiophene, K 38° C., N.

2-(4-[(E)-Hex-4-enoyloxy]phenyl)-5-propylthiophene, K 44° C.

2-(4-[(E)-Hept-2-enoyloxy]phenyl)-5-propylthiophene, K, 17° C., N 29° C., I.

2-(4-[(E)-Oct-2-enoyloxy]phenyl)-5-propylthiophene, K, 21° C., N 42° C., I.

2-(4-[(E)-But-2-enoyloxy]-2-fluorophenyl)-5-propylthiophene.

2-(4-[(E)-Pent-2-enoyloxy]-2-fluorophenyl)-5-propylthiophene.

2-(4-[(E)-Hex-2-enoyloxy]-2-fluorophenyl)-5-propylthiophene.

2-(4-[(E)-Hept-2-enoyloxy]-2-fluorophenyl)-5-propylthiophene.

2-(4-[(E)-Oct-2-enoyloxy]-2-fluorophenyl)-5-propylthiophene.

2-(4-[(E)-But-2-enoyloxy]-3-fluorophenyl)-5-propylthiophene.

2-(4-[(E)-But-2-enoyloxy]phenyl)-5-pentylthiophene, K, 66° C., I.

2-(4-[(E)-Pent-2-enoyloxy]phenyl)-5-pentylthiophene, K, 64° C., I.

2-(4-[(E)-Hept-2-enoyloxy]phenyl)-5-pentylthiophene, K, 37° C., [N 36° C.]I.

2-(4-[(E)-Oct-2-enoyloxy]phenyl)-5-pentylthiophene, K, 44° C., N 49° C., I.

2-(4-[(E)-But-2-enoyloxy]-2-fluorophenyl)-5-pentylthiophene.

2-(4-[(E)-Pent-2-enoyloxy]-2-fluorophenyl)-5-pentylthiophene.

2-(4-[(E)-Hex-2-enoyloxy]-2-fluorophenyl)-5-pentylthiophene.

2-(4-[(E)-Hept-2-enoyloxy]-2-fluorophenyl)-5-pentylthiophene.

2-(4-[(E)-Oct-2-enoyloxy]-2-fluorophenyl)-5-pentylthiophene.

2-(4-[(E)-But-2-enoyloxy]-3-fluorophenyl)-5-pentylthiophene.

2-(4-[(E)-But-2-enoyloxy]lphenyl)-5-methylthiophene.

2-(4-[(E)-Pent-2-enoyloxy]phenyl)-5-methylthiophene.

2-(4-[(E)-Hex-2-enoyloxy]phenyl)-5-methylthiophene, K 87° C.

2-(4-[(E)-But-2-enoyloxy]phenyl)-5-ethylthiophene.

2-(4-[(E)-Pent-2-enoyloxy]phenyl)-5-ethylthiophene.

2-(4-[(E)-Hex-2-enoyloxy]phenyl)-5-ethylthiophene, K 43° C., N 44° C., I.

2-(4-[(E)-Hex-2-enoyloxy]phenyl)-5-butylthiophene, K, 39° C., [N 37° C.], I.

2-(4-[(E)-Hex-2-enoyloxy]phenyl)-5-hexylthiophene, K, 57° C., [N 42° C.], I.

2-(4-[(E)-Hex-2-enoyloxy]phenyl)-5-heptylthiophene, K, 59° C., [N 49° C.], I.

2-(4-[(E)-Hex-2-enoyloxy]phenyl)-5-octylthiophene, K, 65° C., [N 47° C.], I.
2-(4-[(E)-But-2-enoyloxy]biphenyl-4'-yl)-5-methylthiophene.
2-(4-[(E)-But-2-enoyloxy]biphenyl-4'-yl)-5-ethylthiophene.
2-(4-[(E)-But-2-enoyloxy]biphenyl-4'-yl)-5-propylthiophene.
2-(4-[(E)-Pent-2-enoyloxy]biphenyl-4'-yl)-5-propylthiophene.
2-(4-[(E)-Hex-2-enoyloxy]biphenyl-4'-yl)-5-propylthiophene.
2-(4-[(E)-But-2-enoyloxy]biphenyl-4'-yl)-5-butylthiophene.
2-(4-[(E)-But-2-enoyloxy]biphenyl-4'-yl)-5-pentylthiophene.
2-(4-[(E)-Pent-2-enoyloxy]biphenyl-4'-yl)-5-pentylthiophene.
2-(4-[(E)-Hex-2-enoyloxy]biphenyl-4'-yl)-5-pentylthiophene.
2-(4-[(E)-But-2-enoyloxy]biphenyl-4'-yl)-5-hexylthiophene.
2-(4-[(E)-But-2-enoyloxy]biphenyl-4'-yl)-5-heptylthiophene.
2-(4-[(E)-But-2-enoyloxy]biphenyl-4'-yl)-5-octylthiophene.

EXAMPLE 2

Preparation of 2-(4-[(E)-hex-2-Enyloxy]phenyl)-5-pentylthiophene

Triphenylphosphine (0.53 g) was added in small portions to a solution of (E)-hex-2-en-1-ol (0.20 g), 2-(4-hydroxyphenyl)-5-pentylthiophene (0.50 g), diethylazodicarboxylate (0.35 g) in dry tetrahydrofuran (15 cm$^3$) at 0° C. under an atmosphere of nitrogen. The reaction mixture was stirred at room temperature overnight. The solvent was removed under reduced pressure and the crude product was purified by column chromatography on silica gel using a 4:1 petroleum (40–60° C.) ether/ethyl acetate mixture as eluent, followed by recrystallisation from ethanol to yield 0.10 g of 2-(4-[(E)-hex-2-enyloxy]phenyl)-5-pentylthiophene, K, 82° C., I.

The following compounds could be obtained analogously:
2-(4-[(E)-But-2-enyloxy]phenyl)-5-propylthiophene.
2-(4-[(E)-Pent-2-enyloxy]phenyl)-5-propylthiophene.
2-(4-[(E)-Hex-2-enyloxy]phenyl)-5-propylthiophene.
2-(4-[(Z)-Hex-3-enyloxy]phenyl)-5-propylthiophene.
2-(4-[(E)-Hex-4-enyloxy]phenyl)-5-propylthiophene.
2-(4-[(E)-Hept-2-enyloxy]phenyl)-5-propyithiophene.
2-(4-[(E)-Oct-2-enyloxy]phenyl)-5-propylthiophenel.
2-(4-[(E)-But-2-enyloxy]phenyl)-5-pentylthiophene.
2-(4-[(E)-Pent-2-enyloxy]phenyl)-5-pentylthiophene.
2-(4-[(E)-Hept-2-enyloxy]phenyl)-5-pentylthiophene.
2-(4-[(E)-Oct-2-enyloxy]phenyl)-5-pentylthiophene.
2-(4-[(E)-But-2-enyloxy]phenyl)-5-methylthiophene.
2-(4-[(E)-Pent-2-enyloxy]phenyl)-5-methylthiophene.
2-(4-[(E)-Hex-2-enyloxy]phenyl)-5-methylthiophene.
2-(4-[(E)-But-2-enyloxy]phenyl)-5-ethylthiophene.
2-(4-[(E)-Pent-2-enyloxy]phenyl)-5-ethylthiophene.
2-(4-[(E)-Hex-2-enyloxy]phenyl)-5-ethylthiophene.
2-(4-[(E)-Hex-2-enyloxy]phenyl)-5-butylthiophene.
2-(4-[(E)-Hex-2-enyloxy]phenyl)-5-hexylthiophene.
2-(4-[(E)-Hex-2-enyloxy]phenyl)-5-heptylthiophene.
2-(4-[(E)-Hex-2-enyloxy]phenyl)-5-octylthiophenel.
2-(4-[(E)-But-2-enyloxy]biphenyl-4'-yl)-5-methylthiophene.
2-(4-[(E)-But-2-enyloxy]biphenyl4'-yl)-5-ethylthiophene.
2-(4-[(E)-But-2-enyloxy]biphenyl-4'-yl)-5-propylthiophene.
2-(4-[(E)-Pent-2-enyloxy]biphenyl-4'-yl)-5-propylthiophene.
2-(4-[(E)-Hex-2-enyloxy]biphenyl-4'-yl)-5-propylthiophene.
2-(4-[(E)-But-2-enyloxy]biphenyl-4'-yl)-5-butylthiophene.
2-(4-[(E)-But-2-enyloxy]biphenyl-4'-yl)-5-pentylthiophene.
2-(4-[(E)-Pent-2-enyloxy]biphenyl-4'-yl)-5-pentylthiophene.
2-(4-[(E)-Hex-2-enyloxy]biphenyl-4'-yl)-5-pentylthiophene.
2-(4-[(E)-But-2-enyloxy]biphenyl-4'-yl)-5-hexylthiophene.
2-(4-[(E)-But-2-enyloxy]biphenyl-4'-yl)-5-heptylthiophene.
2-(4-[(E)-But-2-enyloxy]biphenyl-4'-yl)-5-octylthiophene.

EXAMPLE 3

Preparation of 2-Cyano-(4-[(E)-hex-2-enoyloxy]phenyl)thiophene

Dicyclohexylcarbodiimide (0.23 g) was added to a solution of 2-cyano-5-(4-hydroxyphenyl)thiophene (0.20 g), (E)-hex-2-enoic acid (0.11 g), 4-(dimethylamino)pyridine (0.02 g) and dichloromethane (40 cm$^3$) at 0° C. under an atmosphere of nitrogen. The reaction mixture was stirred overnight at room temperature, filtered to remove inorganic material and the filtrate evaporated down. The residue was purified by column chromatography on silica gel using dichloromethane as eluent and recrystallisation from ethanol to yield 0.04 g of 2-cyano-(4-[(E)-hex-2-enoyloxy]phenyl) thiophene, K 83° C., [N 82° C.], I.

The 2-cyano-5-(4-hydroxyphenyl)thiophene required as starting material could be prepared as follows:

A solution of 2-cyanothiophene (30.0 g), anhydrous pyridine hydrobromide (100 cm$^3$) and nitroethane (13.5 g) was heated under reflux for 1 h under an atmosphere of nitrogen. The cooled reaction mixture was poured onto a mixture of chloroform (300 cm$^3$) and 0.1M hydrochloric acid (300 cm$^3$). The organic layer was separated off and the aqueous layer extracted with dichloromethane (2×50 cm$^3$). The combined organic layers were washed with brine (2×100 cm$^3$), dried (MgSO$_4$), filtered and then evaporated down. The residue was purified by column chromatography on silica gel using a 1:1 hexane/dichloromethane mixture as eluent to yield 12.8 g of 2-bromo-5-cyanothiophene as an oil.

A solution of 2-bromo-5-cyanothiophene (4.9 g), 4-methoxyphenyl boronic acid (4.7 g), 2M aqueous sodium carbonate solution (80 cm$^3$), tetrakis(triphenylphosphine) palladium (0) (0.4 g) and dimethoxyethane (80 cm$^3$) was heated under reflux for 6 h under an atmosphere of nitrogen.

20% Hydrochloric acid (200 cm³) was added and the resultant mixture extracted with diethyl ether (5×100 cm³). The combined organic layers were washed with 20% hydrochloric acid (1×100 cm³), brine (2×100 cm³) and then dried (MgSO$_4$), filtered and evaporated down. The residue was purified by column chromatography on silica gel using a 9:1 hexane/ethyl acetate mixture as eluent and recrystallisation from ethanol to yield 4.5 g of 2-cyano-5-(4-methoxyphenyl) thiophene, K 58–60° C., I.

A 1M solution of boron tribromide in dichloromethane (55 cm³) was added dropwise to a solution of 2-cyano-5-(4-methoxyphenyl)thiophene (2.3 g) and dichloromethane (80 cm³) at 0° C. under an atmosphere of nitrogen. The reaction solution was stirred overnight and water (100 cm³) added. The organic layer was separated off and the aqueous layer extracted with dichloromethane (2×100 cm³). The combined organic layers were washed with brine (2×100 cm³) and then dried (MgSO$_4$), filtered and evaporated down. The residue was purified by column chromatography on silica gel using a 9:1 hexane/ethyl acetate mixture as eluent and recrystallisation from ethanol to yield 1.4 g of g 2-cyano-5-(4-hydroxyphenyl)thiophene.

The following compounds could be obtained analogously:

2-(4-[(E)-But-2-enoyloxy]phenyl)-5-cyanothiophene.

2-Cyano-(4-[(E)-pent-2-enoyloxy]phenyl)thiophene.

2-Cyano-(4-[(Z)-hex-3-enoyloxy]phenyl)thiophene, K 53° C., I.

2-Cyano-(4-[(E)-hex-4-enoyloxy]phenyl)thiophene, K 74° C., [N 39° C.], I.

2-Cyano-(4-[(E)-hept-2-enoyloxy]phenyl)thiophene.

2-Cyano-(4-[(E)-oct-2-enoyloxy]phenyl)thiophene.

2-(4-[(E)-But-2-enoyloxy]biphenyl-4'-yl)-5-cyanothiophene.

2-Cyano-5-(4-[(E)-pent-2-enyloxy]biphenyl-4'-yl)thiophene.

2-Cyano-5-(4-[(E)-hex-2-enoyloxy]biphenoyl-4'-oyl)thiophene.

2-Cyano-5-(4-[(Z)-hex-3-enyloxy]biphenoyl-4'-yl)thiophene.

2-Cyano-5-(4-[(E)-hex-4-enoyloxy]biphenoyl-4'-yl)thiophene.

2-Cyano-5-(4-[(E)-hept-2-enoyloxy]biphenyl-4'-yl)thiophene.

2-Cyano-5-(4-[(E)-oct-2-enoyloxy]biphenoyl-4'-yl)thiophene.

EXAMPLE 4

Preparation of 2-Cyano-5-(4-[(E)-hex-2-enyloxy]phenyl)thiophene

Triphenylphosphine (0.95 g) was added in small portions to a solution of (E)-hex-2-en-1-ol (0.40 g), 2-cyano-5-(4-hydroxyphenyl)thiophene (0.71 g), diethylazodicarboxylate (0.63 g) in dry tetrahydrofuran (40 cm³) at 0° C. under an atmosphere of nitrogen. The reaction mixture was stirred at room temperature overnight. The solvent was removed under reduced pressure and the crude product was purified by column chromatography on silica gel using a 4:1 petroleum (40–60° C.) ether/ethyl acetate mixture as eluent, followed by recrystallisation from ethanol to yield 0.19 g of 2-cyano-5-(4-[(E)-hex-2-enyloxy]phenyl)thiophene.

The following compounds could be obtained analogously:

2-(4-[(E)-But-2-enyloxy]phenyl)-5-cyanothiophene.

2-Cyano-5-(4-[(E)-pent-2-enyloxy]phenyl)thiophene.

2-Cyano-5-(4-[(E)-hex-2-enyloxy]phenyl)thiophene.

2-Cyano-5-(4-[(Z)-hex-3-enyloxy]phenyl)thiophene.

2-Cyano-5-(4-[(E)-hex-4-enyloxy]phenyl)thiophene.

2-Cyano-5-(4-[(E)-hept-2-enyloxy]phenyl)thiophene.

2-Cyano-5-(4-[(E)-oct-2-enyloxy]phenyl)thiophene.

2-(4-[(E)-But-2-enyloxy]biphenyl-4'-yl)-5-cyanothiophene.

2-Cyano-5-(4-[(E)-pent-2-enyloxy]biphenyl-4'-yl)thiophene.

2-Cyano-5-(4-[(E)-hex-2-enyloxy]biphenyl-4'-yl)thiophene.

2-Cyano-5-(4-[(Z)-hex-3-enyloxy]biphenyl-4'-yl)thiophene.

2-Cyano-5-(4-[(E)-hex4-enyloxy]biphenyl-4'-yl)thiophene.

2-Cyano-5-(4-[(E)-hept-2-enyloxy]biphenyl-4'-yl)thiophene.

2-Cyano-5-(4-[(E)-oct-2-enyloxy]biphenyl-4'-yl)thiophene.

EXAMPLE 5

Preparation of 2-(4-[(E)-hex-2-Enoyloxy]phenyl)-5-octylthiazole

Dicyclohexylcarbodiimide (0.2 g) is added to a solution of 2-(4-hydroxyphenyl)-5-octylthiazole (0.25 g), (E)-hex-2-enoic acid, (0.1 g) 4-(dimethylamino)pyridine (0.05 g) and dichloromethane (20 cm³) at 0° C. under an atmosphere of nitrogen. The reaction mixture is stirred overnight at room temperature, filtered to remove inorganic material and the filtrate evaporated down. The residue is purified by column chromatography on silica gel using hexane/ethyl acetate (9/1 v/v) as eluent and recrystallisation from hexane to yield 0.15 g of 2-(4-[(E)-hex-2-enoyloxy]phenyl)-5-octylthiazole.

The 2-(4-hydroxyphenyl)-5-octylthiazole required as starting material could be prepared as follows:

A 1M solution of boron tribromide in dichloromethane (50 cm³) is added dropwise to a solution of 2-(4-ethoxyphenyl)-5-octylthiazole [J. prakt. Chem., (1979) Vol. 321, pp 643](2.0 g) and dichloromethane (50 cm³) at 0° C. under an atmosphere of nitrogen. The reaction solution is stirred overnight and water (100 cm³) added. The organic layer is separated off and the aqueous layer extracted with dichloromethane (2×100 cm³). The combined organic layers are washed with brine (2×100 cm³) and then dried (MgSO$_4$), filtered and evaporated down. The residue is purified by column chromatography on silica gel using a 9:1 hexane/ethyl acetate mixture as eluent and recrystallisation from ethanol to yield 1.0 9 of g 2-(4-hydroxyphenyl)-5-octylthiazole.

The following compounds could be obtained analogously:

2-(4-[(E)-But-2-enoyloxy]phenyl)-5-propylthiazole.

2-(4-[(E)-Pent-2-enoyloxy]phenyl)-5-propylthiazole.

2-(4-[(E)-Hex-2-enoyloxy]phenyl)-5-propylthiazole.

2-(4-[(Z)-Hex-3-enoyloxy]phenyl)-5-propylthiazole.

2-(4-[(E)-Hex-4-enoyloxy]phenyl)-5-propylthiazole.

2-(4-[(E)-Hept-2-enoyloxy]phenyl)-5-propylthiazole.

2-(4-[(E)-Oct-2-enoyloxy]phenyl)-5-propylthiazole.

2-(4-[(E)-But-2-enoyloxy]phenyl)-5-pentylthiazole.

2-(4-[(E)-Pent-2-enoyloxy]phenyl)-5-pentylthiazole.

2-(4-[(E)-Hept-2-enoyloxy]phenyl)-5-pentylthiazole.

2-(4-[(E)-Oct-2-enoyloxy]phenyl)-5-pentylthiazole.

2-(4-[(E)-But-2-enoyloxy]phenyl)-5-methylthiazole.
2-(4-[(E)-Pent-2-enoyloxy]phenyl)-5-methylthiazole.
2-(4-[(E)-Hex-2-enoyloxy]phenyl)-5-methylthiazole.
2-(4-[(E)-But-2-enoyloxy]phenyl)-5-ethylthiazole.
2-(4-[(E)-Pent-2-enoyloxy]phenyl)-5-ethylthiazole.
2-(4-[(E)-Hex-2-enoyloxy]phenyl)-5-ethylthiazole.
2-(4-[(E)-Hex-2-enoyloxy]phenyl)-5-butylthiazole.
2-(4-[(E)-Hex-2-enoyloxy]phenyl)-5-hexylthiazole.
2-(4-[(E)-Hex-2-enoyloxy]phenyl)-5-heptylthiazole.
2-(4-[(E)-Hex-2-enoyloxy]phenyl)-5-octylthiazole.
2-(4-[(E)-But-2-enoyloxy]biphenyl-4'-yl)-5-propylthiazole.
2-(4-[(E)-Pent-2-enoyloxy]biphenyl-4'-yl)-5-propylthiazole.
2-(4-[(E)-Hex-2-enoyloxy]biphenyl-4'-yl)-5-propylthiazole.
2-(4-[(Z)-Hex-3-enoyloxy]biphenyl-4'-yl)-5-propylthiazole.
2-(4-[(E)-Hex-4-enoyloxy]biphenyl-4'-yl)-5-propylthiazole.
2-(4-[(E)-Hept-2-enoyloxy]biphenyl-4'-yl)-5-propylthiazole.
2-(4-[(E)-Oct-2-enoyloxy]biphenyl-4'-yl)-5-propylthiazole.
2-(4-[(E)-But-2-enoyloxy]biphenyl-4'-yl)-5-butylthiazole.
2-(4-[(E)-But-2-enoyloxy]biphenyl-4'-yl)-5-pentylthiazole.
2-(4-[(E)-Pent-2-enoyloxy]biphenyl-4'-yl)-5-pentylthiazole.
2-(4-[(E)-Hex-2-enoyloxy]biphenyl-4'-yl)-5-pentylthiazole.
2-(4-[(Z)-Hex-3-enoyloxy]biphenyl-4'-yl)-5-pentylthiazole.
2-(4-[(E)-Hex-4-enoyloxy]biphenyl-4'-yl)-5-pentylthiazole.
2-(4-[(E)-Hept-2-enoyloxy]biphenyl-4'-yl)-5-pentylthiazole.
2-(4-[(E)-Oct-2-enoyloxy]biphenyl-4'-yl)-5-pentylthiazole.
2-(4-[(E)-But-2-enoyloxy]biphenyl-4'-yl)-5-hexylthiazole.
2-(4-[(E)-But-2-enoyloxy]biphenyl-4'-yl)-5-heptylthiazole.
2-(4-[(E)-But-2-enoyloxy]biphenyl-4'-yl)-5-octylthiazole.

EXAMPLE 6

Preparation of 2-(4-[(E)-hex-2-Enyloxy]phenyl)-5-octylthiazole

Triphenylphosphine (0.95 g) is added in small portions to a solution of (E)-hex-2-en-1-ol (0.40 g), 2-(4-hydroxyphenyl)-5-octylthiazole (0.70 g), diethylazodicarboxylate (0.60 g) in dry tetrahydrofuran (40 cm³) at 0° C. under an atmosphere of nitrogen. The reaction mixture is stirred at room temperature overnight. The solvent is removed under reduced pressure and the crude product was purified by column chromatography on silica gel using a 4:1 petroleum (40–60° C.) ether/ethyl acetate mixture as eluent, followed by recrystallisation from ethanol to yield 0.15 g of 2-(4-[(E)-hex-2-enyloxy]phenyl)-5-octyfthiazole.

The following compounds could be obtained analogously:
2-(4-[(E)-But-2-enyloxy]phenyl)-5-propylthiazole.
2-(4-[(E)-Pent-2-enyloxy]phenyl)-5-propylthiazole.
2-(4-[(E)-Hex-2-enyloxy]phenyl)-5-propylthiazole.
2-(4-[(Z)-Hex-3-enyloxy]phenyl)-5-propylthiazole.
2-(4-[(E)-Hex-4-enyloxy]phenyl)-5-propylthiazole.
2-(4-[(E)-Hept-2-enyloxy]phenyl)-5-propylthiazole.
2-(4-[(E)-Oct-2-enyloxy]phenyl)-5-propylthiazole.
2-(4-[(E)-But-2-enyloxy]phenyl)-5-pentytthiazole.
2-(4-[(E)-Pent-2-enyloxy]phenyl)-5-pentylthiazole.
2-(4-[(E)-Hept-2-enyloxy]phenyl)-5-pentylthiazole.
2-(4-[(E)-Oct-2-enyloxy]phenyl)-5-pentylthiazole.
2-(4-[(E)-But-2-enyloxy]phenyl)-5-methylthiazole.
2-(4-[(E)-Pent-2-enyloxy]phenyl)-5-methylthiazole.
2-(4-[(E)-Hex-2-enyloxy]phenyl)-5-methylthiazole.
2-(4-[(E)-But-2-enyloxy]phenyl)-5-ethylthiazole.
2-(4-[(E)-Pent-2-enyloxy]phenyl)-5-ethylthiazole.
2-(4-[(E)-Hex-2-enyloxy]phenyl)-5-ethylthiazole.
2-(4-[(E)-Hex-2-enyloxy]phenyl)-5-butylthiazole.
2-(4-[(E)-Hex-2-enyloxy]phenyl)-5-hexylthiazole
2-(4-[(E)-Hex-2-enyloxy]phenyl)-5-heptylthiazole.
2-(4-[(E)-Hex-2-enyloxy]phenyl)-5-octylthiazole.
2-(4-[(E)-But-2-enyloxy]biphenyl-4'-yl)-5-propylthiazole.
2-(4-[(E)-Pent-2-enyloxy]biphenyl-4'-yl)-5-propylthiazoie.
2-(4-[(E)-Hex-2-enytoxy]biphenyl-4'-yl)-5-propylthiazole.
2-(4-[(Z)-Hex-3-enyloxy]biphenyl-4'-yl)-5-propylthiazole.
2-(4-[(E)-Hex-4-enyloxy]biphenyl-4'-y)-5-propylthiazole.
2-(4-[(E)-Hept2-enyloxy]biphenytA'-yl)-5-propylthiazole.
2-(4-[(E)-Oct-2-enyloxy]biphenyl-4'-yl)-5-propylthiazole.
2-(4-[(E)-But-2-enyloxy]biphenyl-4'-yl)-5-butylthiazole.
2-(4-[(E)-But-2-enyloxy]biphenyl-4'-yl)-5-pentylthiazole.
2-(4-[(E)-Pent-2-enyloxy]biphenyl-4'-yl)-5-pentylthiazole.
2-(4-[(E)-Hex-2-enyloxy]biphenyl-4'-yl)-5-pentylthiazole.
2-(4-[(Z)-Hex-3-enyloxy]biphenyl-4'-yl)-5-pentylthiazole.
2-(4-[(E)-Hex-4-enyloxy]biphenyl-4'-yl)-5-pentylthiazoie.
2-(4-[(E)-Hept-2-enyloxy]biphenyl-4'-yl)-5-pentylthiazole.
2-(4-[(E)-Oct-2-enyloxy]biphenyl-4'-yl)-5-pentylthiazole.
2-(4-[(E)-But-2-enyloxy]biphenyl-4'-yl)-5-hexylthiazole.
2-(4-[(E)-But-2-enyloxy]biphenyl-4'-yl)-5-heptylthiazole.
2-(4-[(E)-But-2-enyloxy]biphenyl-4'-yl)-5-octylthiazole.

EXAMPLE 7

Preparation of 2-(4-[(E)-hex-2-Enoyloxy]phenyl)-5-pentyl-1,3,4-thiadiazole

Dicyclohexylcarbodiimide (0.2 g) is added to a solution of 2-(4-hydroxyphenyl)-5-pentyl-1,3,4-thiadiazole [Mol.

Cryst. Liq. Cryst., (1990) Vol., 191, pp 223] (0.25 g), (E)-hex-2-enoic acid, (0.1 g) 4-(dimethylamino)pyridine (0.05 g) and dichloromethane (20 cm$^3$) at 0° C. under an atmosphere of nitrogen. The reaction mixture is stirred overnight at room temperature, filtered to remove inorganic material and the filtrate evaporated down. The residue is purified by column chromatography on silica gel using hexane/ethyl acetate (9/1 v/v) as eluent and recrystallisation from hexane to yield 0.17 g of 2-(4-[(E)-hex-2-enoyloxy] phenyl)-5-pentyl-1,3,4-thiadiazole.

The following compounds could be obtained analogously:

2-(4-[(E)-But-2-enoyloxy]phenyl)-5-propyl-1,3,4-thiadiazole.
2-(4-[(E)-Pent-2-enoyloxy]phenyl)-5-propyl-1,3,4-thiadiazole.
2-(4-[(E)-Hex-2-enoyloxy]phenyl)-5-propyl-1,3,4-thiadiazole.
2-(4-[(Z)-Hex-3-enoyloxy]phenyl)-5-propyl-1,3,4-thiadiazole.
2-(4-[(E)-Hex-4-enoyloxy]phenyl)-5-propyl-1,3,4-thiadiazole.
2-(4-[(E)-Hept-2-enoyloxy]phenyl)-5-propyl-1,3,4-thiadiazole.
2-(4-[(E)-Oct-2-enoyloxy]phenyl)-5-propyl-1,3,4-thiadiazole.
2-(4-[(E)-But-2-enoyloxy]phenyl)-5-pentyl-1,3,4-thiadiazole.
2-(4-[(E)-Pent-2-enoyloxy]phenyl)-5-pentyl-1,3,4-thiadiazole.
2-(4-[(E)-Hept-2-enoyloxy]phenyl)-5-pentyl-1,3,4-thiadiazole.
2-(4-[(E)-Oct-2-enoyloxy]phenyl)-5-pentyl-1,3,4-thiadiazole.
2-(4-[(E)-But-2-enoyloxy]phenyl)-5-methyl-1,3,4-thiadiazole.
2-(4-[(E)-Pent-2-enoyloxy]phenyl)-5-methyl-1,3,4-thiadiazole.
2-(4-[(E)-Hex-2-enoyloxy]phenyl)-5-methyl-1,3,4-thiadiazole.
2-(4-[(E)-But-2-enoyloxy]phenyl)-5-ethyl-1,3,4-thiadiazole.
2-(4-[(E)-Pent-2-enoyloxy]phenyl)-5-ethyl-1,3,4-thiadiazole.
2-(4-[(E)-Hex-2-enoyloxy]phenyl)-5-ethyl-1,3,4-thiadiazole.
2-(4-[(E)-Hex-2-enoyloxy]phenyl)-5-butyl-1,3,4-thiadiazole.
2-(4-[(E)-Hex-2-enoyloxy]phenyl)-5-hexyl-1,3,4-thiadiazole.
2-(4-[(E)-Hex-2-enoyloxy]phenyl)-5-heptyl-1,3,4-thiadiazole.
2-(4-[(E)-Hex-2-enoyloxy]phenyl)-5-octyl-1,3,4-thiadiazole.
2-(4-[(E)-But-2-enoyloxy]biphenyl-4-yl)-5-propyl-1,3,4-thiadiazoie.
2-(4-[(E)-Pent-2-enoyloxy]biphenyl-4'-yl)-5-propyl-1,3,4-thiadiazole.
2-(4-[(E)-Hex-2-enoyloxy]biphenyl-4'-yl)-5-propyl-1,3,4-thiadiazole.
2-(4-[(Z)-Hex-3-enoyloxy]biphenyl-4'-yl)-5-propyl-1,3,4-thiadiazole.
2-(4-[(E)-Hex-4-enoyloxy]biphenyl-4'-yl)-5-propyl-1,3,4-thiadiazole.
2-(4-[(E)-Hept-2-enoyloxy]biphenyl-4'-yl)-5-propyl-1,3,4-thiadiazole.
2-(4-[(E)-Oct-2-enoyloxy]biphenyl-4'-yl)-5-propyl-1,3,4-thiadiazole.
2-(4-[(E)-But-2-enoyloxy]biphenyl-4'-yl)-5-butyl-1,3,4-thiadiazole.
2-(4-[(E)-But-2-enoyloxy]biphenyl-4'-yl)-5-pentyl-1,3,4-thiadiazole.
2-(4-[(E)-But-2-enoyloxy]biphenyl-4'-yl)-5-pentyl-1,3,4-thiadiazole.
2-(4-[(E)-Pent-2-enoyloxy]biphenyl-4'-yl)-5-pentyl-1,3,4-thiadiazole.
2-(4-[(E)-Hex-2-enoyloxy]biphenyl-4'-yl)-5-pentyl-1,3,4-thiadiazole.
2-(4-[(E)-Hex-2-enoyloxy]biphenyl-4'-yl)-5-pentyl-1,3,4-thiadiazole.
2-(4-[(E)-Hex-4-enoyloxy]biphenyl-4'-yl)-5-pentyl-1,3,4-thiadiazole.
2-(4-[(E)-Het-2-enoyloxy]biphenyl-4'-yl)-5-pentyl-1,3,4-thiadiazole.
2-(4-[(E)-Oct-2-enoyloxy]biphenyl-4'-yl)-5-pentyl-1,3,4-thiadiazole.
2-(4-[(E)-But-2-enoyloxy]biphenyl-4'-yl)-5-hextyl-1,3,4-thiadiazole.
2-(4-[(E)-But-2-enoyloxy]biphenyl-4'-yl)-5-heptyl-1,3,4-thiadiazole. 2-(4-[(E)-But-2-enoyloxy]biphenyl-4'-yl)-5-octyl-1,3,4-thiadiazole.

EXAMPLE 8

Preparation of 2-(4-[(E)-hex-2-Enyloxy]phenyl)-5-pentyl-1,3,4-thiadiazole

Triphenylphosphine (0.95 g) is added in small portions to a solution of (E)-hex-2-en-1-ol (0.40 g), 2-(4-hydroxyphenyl)-5-pentyl-1,3,4-thiadiazole (0.71 g), diethylazodicarboxylate (0.63 g) in dry tetrahydrofuran (40 cm$^3$) at 0° C. under an atmosphere of nitrogen. The reaction mixture is stirred at room temperature overnight. The solvent is removed under reduced pressure and the crude product was purified by column chromatography on silica gel using a 4:1 petroleum (40–60° C.) ether/ethyl acetate mixture as eluent, followed by recrystallisation from ethanol to yield 0.19 g of 2-(4-[(E)-hex-2-enyloxy]phenyl)-5-pentyl-1,3,4-thiadiazole.

The following compounds could be obtained analogously:

2-(4-[(E)-But-2-enyloxy]phenyl)-5-propyl-1,3,4-thiadiazole.
2-(4-[(E)-Pent-2-enyloxy]phenyl)-5-propyl-1,3,4-thiadiazole.
2-(4-[(E)-Hex-2-enyloxy]phenyl)-5-propyl-1,3,4-thiadiazole.
2-(4-[(Z)-Hex-3-enyloxy]phenyl)-5-propyl-1,3,4-thiadiazole.
2-(4-[(E)-Hex-4-enyloxy]phenyl)-5-propyl-1,3,4-thiadiazole.
2-(4-[(E)-Hept-2-enyloxy]phenyl)-5-propyl-1,3,4-thiadiazole.
2-(4-[(E)-Oct-2-enyloxy]phenyl)-5-propyl-1,3,4-thiadiazole.
2-(4-[(E)-But-2-enyloxy]phenyl)-5-pentyl-1,3,4-thiadiazole.
2-(4-[(E)-Pent-2-enyloxy]phenyl)-5-pentyl-1,3,4-thiadiazole.

2-(4-[(Z)-Hex-3-enyloxy]phenyl)-5-pentyl-1,3,4-thiadiazole.
2-(4-[(E)-Hex-4-enyloxy]phenyl)-5-pentyl-1,3,4-thiadiazole.
2-(4-[(E)-Hept-2-enyloxy]phenyl)-5-pentyl-1,3,4-thiadiazole.
2-(4-[(E)-Oct-2-enyloxy]phenyl)-5-pentyl-1,3,4-thiadiazole.
2-(4-[(E)-But-2-enyloxy]pheny)-5-methyl-1,3,4-thiadiazole.
2-(4-[(E)-Pent-2-enyloxy]phenyl)-5-methyl-1,3,4-thiadiazole.
2-(4-[(E)-Hex-2-enyloxy]phenyl)-5-methyl-1,3,4-thiadiazole.
2-(4-[(E)-But-2-enyloxy]phenyl)-5-ethyl-1,3,4-thiadiazole.
2-(4-[(E)-Pent-2-enyloxy]phenyl)-5-ethyl-1,3,4-thiadiazole.
2-(4-[(E)-Hex-2-enyloxy]phenyl)-5-ethyl-1,3,4-thiadiazole.
2-(4-[(E)-Hex-2-enyloxy]phenyl)-5-butyl-1,3,4-thiadiazole.
2-(4-[(E)-Hex-2-enyloxy]phenyl)-5-hexy(-1,3,4-thiadiazole.
2-(4-[(E)-Hex-2-enyloxy]phenyl)-5-heptyl-1,3,4-thiadiazole.
2-(4-[(E)-Hex-2-enyloxy]phenyl)-5-octyl-1,3,4-thiadiazole.
2-(4-[(E)-But-2-enyloxy]biphenyl-4'-yl)-5-propyl-1,3,4-thiadiazole.
2-(4-[(E)-Pent-2-enyloxy]biphenyl-4'-yl)-5-propy 1,3,4-thiadiazole.
2-(4-[(E)-Hex-2-enyloxy]biphenyl-4'-yl)-5-propyl-1,3,4-thiadiazole.
2-(4-[(Z)-Hex-3-enyloxy]biphenyl-4'-yl)-5-propyl-1,3,4-thiadiazole.
2-(4-[(E)-Hex-4-enyloxy]biphenyl-4'-yl)-5-propyl-1,3,4-thiadiazole.
2-(4-[(E)-Hept-2-enyloxy]biphenyl-4'-yl)-5-propyl-1,3,4-thiadiazole.
2-(4-[(E)-Oct-2-enyloxy]biphenyl-4'-yl)-5-propyl-1,3,4-thiadiazole.
2-(4-[(E)-But-2-enyloxy]biphenyl-4'-yl)-5-butyl-1,3,4-thiadiazole.
2-(4-[(E)-But-2-enytoxy]biphenyl-4'-yl)-5-pentyl-1,3,4-thiadiazole.
2-(4-[(E)-Pent-2-enyloxy]biphenyl-4'-yl)-5-pentyl-1,3,4-thiadiazole.
2-(4-[(E)-Hex-2-enyloxy]biphenyl-4'-yl)-5-pentyl-1,3,4-thiadiazole.
2-(4-[(Z)-Hex-3-enyloxy]biphenyl-4'-yl)-5-pentyl-1,3,4-thiadiazole.
2-(4-[(E)-Hex-4-enyloxy]biphenyl-4'-yl)-5-pentyl-1,3,4-thiadiazole.
2-(4-[(E)-Hept-2-enyloxy]biphenyl-4'-yl)-5-pentyl-1,3,4-thiadiazole.
2-(4-[(E)-Oct-2-enyloxy]biphenyl-4'-yl)-5-pentyl-1,3,4-thiadiazole.
2-(4-[(E)-But-2-enyloxy]biphenyl-4'-yl)-5-hexyl-1,3,4-thiadiazole.
2-(4-[(E)-But-2-enyloxy]biphenyl-4'-yl)-5-heptyl-1,3,4-thiadiazole.
2-(4-[(E)-But-2-enyloxy]biphenyl-4'-yl)-5-octyl-1,3,4-thiadiazole.

EXAMPLE 9

Preparation of 2,5-bis(4-[(E)-hex-2-Enoyloxy] phenyl)-1,3,4-thiadiazole

Dicyclohexylcarbodiimide (0.4 g) is added to a solution of 2,5-bis(4-hydroxyphenyl)-1,3,4-thiadizole (0.25 g), (E)-hex-2-enoic acid, (0.2 g) 4-(dimethylamino)pyridine (0.10 9) and dichloromethane (50 cm$^3$) at 0° C. under an atmosphere of nitrogen. The reaction mixture is stirred overnight at room temperature, filtered to remove inorganic material and the filtrate evaporated down. The residue is purified by column chromatography on silica gel using hexane/ethyl acetate (9/1 v/v) as eluent and recrystallisation from hexane to yield 0.16 g of 2,5-bis(4-[(E)-hex-2-enoyloxy]phenyl)-1,3,4-thiadiazole.

The 2,5-bis(4-hydroxyphenyl)-1,3,4-thiadizole required as starting material could be prepared as follows:

A 1M solution of boron tribromide in dichloromethane (100 cm$^3$) is added dropwise to a solution of 2,5-bis(4-methoxyphenyl)-1,3,4-thiadiazole [J. prakt. Chem., (1 980) Vol. 322, pp. 933] (2.0 g) and dichloromethane (50 cm$^3$) at 0° C. under an atmosphere of nitrogen. The reaction solution is stirred overnight and water (100 cm$^3$) added. The organic layer is separated off and the aqueous layer extracted with dichloromethane (2×100 cm$^3$). The combined organic layers are washed with brine (2×100 cm$^3$) and then dried (MgSO$_4$), filtered and evaporated down. The residue is purified by column chromatography on silica gel using a 9:1 hexanelethyl acetate mixture as eluent and recrystallisation from ethanol to yield 1.0 g of g 2,5-bis(4-hydroxyphenyl)-1,3,4-thiadiazole.

The following compounds could be obtained analogously:
2,5-bis(4-[(E)-But-2-enoyloxy]phenyl)-1,3,4-thiadiazole.
2,5-bis(4-[(E)-Pent-2-enoyloxy]phenyl)-1,3,4-thiadiazole.
2,5-bis(4-[(Z)-Hex-3-enoyloxy]phenyl)-1,3,4-thiadiazole.
2,5-bis(4-[(E)-Hex-4-enoyloxy]phenyl)-1,3,4-thiadiazole.
2,5-bis(4-[(E)-Hept-2-enoyloxy]phenyl)-1,3.4-thiadiazole.
2,5-bis(4-[(E)-Oct-2-enoyloxy]phenyl)-1,3,4-thiadiazoie.
2,5-bis(4-[(E)-But-2-enoyloxy]phenyl)-thiazole.
2,5-bis(4-[(E)-Pent-2-enoyloxy]phenyl)thiazole.
2,5-bis(4-[(E)-Hex-2-enoyloxy]phenyl)thiazole.
2,5-bis(4-[(E)-Hept-2-enoyloxy]phenyl)thiazole.
2,5-bis(4-[(E)-Oct-2-enoyloxy]phenyl)thiazole.
2,5-bis(4-[(E)-But-2-enoyloxy]phenyl)thiophene.
2,5-bis(4-[(E)-Pent-2-enoyloxy]phenyl)thiophene.
2,5-bis(4-[(E)-Hex-2-enoyloxy]phenyl)thiophene,
2,5-bis(4-[(E)-Hept-2-enoyloxy]phenyl)thiophene.
2,5-bis(4-[(E)-Oct-2-enoyloxy]phenyl)thiophene.
2,5-bis(4-[(E)-But-2-enoyloxy]phenyl)-1,3,4-oxadiazole.
2,5-bis(4-[(E)-Pent-2-enoyloxy]phenyl)-1,3,4-oxadiazole.
2,5-bis(4-[(Z)-Hex-3-enoyloxy]phenyl)-1,3,4-oxadiazole.
2,5-bis(4-[(E)-Hex.-enoyloxy]phenyl)-1,3,4-oxadiazole.
2,5-bis(4-[(E)-Hept-2-enoyloxy]phenyl)-1,3,4-oxadiazole.
2,5-bis(4-[(E)-Oct-2-enoyloxy]phenyl)-1,3,4-oxadiazole.
2,5-bis(4-[(E)-But-2-enoyloxy]phenyl)-oxazole.

2,5-bis(4-[(E)-Pent-2-enoyloxy]phenyl) oxazole.
2,5-bis(4-[(E)-Hex-2-enoyloxy]phenyl)oxazole.
2,5-bis(4-[(E)-Hept-2-enoyloxy]phenyl)oxazole.
2,5-bis(4-[(E)-Oct-2-enoyloxy]phenyl)oxazole.
2,5-bis(4-[(E)-But-2-enoyloxy]phenyl)furan.
2,5-bis(4-[(E)-Pent-2-enoyloxy]phenyl)furan.
2,5-bis(4-[(E)-Hex-2-enoyloxy]phenyl)furan.
2,5-bis(4-[(E)-Hept-2-enoyloxy]phenyl)furan.
2,5-bis(4-[(E)-Oct-2-enoyloxy]phenyl)furan.

EXAMPLE 10

Preparation of 2,5-bis(4-[(E)-hex-2-Enyloxy]phenyl)-1,3,4-thiadiazoie

Triphenylphosphine (2.0 g) is added in small portions to a solution of (E)-hex-2-en-1-ol (0.80 g), 2,5-bis(4-hydroxyphenyl)-1,3,4-thiadizole (0.70 g), diethylazodicarboxylate (1.20 g) in dry tetrahydrofuran (100 cm$^3$) at 0° C. under an atmosphere of nitrogen. The reaction mixture is stirred at room temperature overnight. The solvent is removed under reduced pressure and the crude product was purified by column chromatography on silica gel using a 4:1 petroleum (40–60° C.) ether/ethyl acetate mixture as eluent, followed by recrystallisation from ethanol to yield 0.12 g of 2,5-bis(4-[(E)-hex-2-enyloxy]phenyl)-1,3,4-thiadiazole.

The following compounds could be obtained analogously:
2,5-bis(4-[(E)-But-2-enyloxy]phenyl)-1,3,4-thiadiazole.
2,5-bis(4-[(E)-Pent-2-enyloxy]phenyl)-1,3,4-thiadiazole.
2,5-bis(4-[(Z)-Hex-3-enyloxy]phenyl)-1,3,4-thiadiazole.
2,5-bis(4-[(E)-Hex-4-enyloxy]phenyl)-I,3,4-thiadiazole.
2,5-bis(4-[(E)-Hept-2-enyloxy]phenyl)-1,3,4-thiadiazole.
2,5-bis(4-[(E)-Oct-2-enyloxy]phenyl)-1,3,4-thiadiazole.
2,5-bis(4-[(E)-But-2-enyloxy]phenyl)thiazole.
2,5-bis(4-[(E)-Pent-2-enyloxy]phenyl)thiazole.
2,5-bis(4-[(E)-Hex-2-enyloxy]phenyl) thiazole.
2,5-bis(4-[(E)-Hept-2-enyloxy]phenyl)thiazole.
2,5-bis(4-[(E)-Oct-2-enyloxy]phenyl)thiazole.
2,5-bis(4-[(E)-But-2-enyloxy]phenyl)thiophene.
2,5-bis(4-[(E)-Pent-2-enyloxy]phenyl)thiophene.
2,5-bis(4-[(E)-Hex-2-enyloxy]phenyl)thiophene.
2,5-bis(4-[(E)-Hept-2-enyloxy]phenyl)thiophene.
2,5-bis(4-[(E)-Oct-2-enyloxy]phenyl)thiophene.
2,5-bis(4-[(E)-But-2-enyloxy]phenyl)-1,3,4-oxadiazole.
2,5-bis(4-[(E)-Pent-2-enyloxy]phenyl)-1,3,4-oxadiazole.
2,5-bis(4-[(Z)-Hex-3-enyloxy]phenyl)-1,3,4-oxadiazole
2,5-bis(4-[(E)-Hex-4-enyloxy]phenyl)-1,3,4-oxadiazole
2,5-bis(4-[(E)-Hept-2-enyloxy]phenyl)-1,3,4-oxadiazole.
2,5-bis(4-[(E)-Oct-2-enyloxy]phenyl)-1,3,4-oxadiazole.
2,5-bis(4-[(E)-But-2-enyloxy]phenyl)oxazole.
2,5-bis(4-[(E)-Pent-2-enyloxy]phenyl)oxazole.
2,5-bis(4-[(E)-Hex-2-enyloxy]phenyl)oxazole.
2,5-bis(4-[(E)-Hept-2-enyloxy]phenyl)oxazole.
2,5-bis(4-[(E)-Oct-2-enyloxy]phenyl)oxazole.
2,5-bis(4-[(E)-But-2-enyloxy]phenyl)furan.
2,5-bis(4-[(E)-Pent-2-enyloxy]phenyl)furan.
2,5-bis(4-[(E)-Hex-2-enyloxy]phenyl)furan.
2,5-bis(4-[(E)-Hept-2-enyloxy]phenyl)furan.
2,5-bis(4-[(E)-Oct-2-enyloxy]phenyl)furan.

EXAMPLE 11

Preparation of 2-[(E)-hex-2-Enyloxy]-5-(4'-hexylbiphenyl-4-yl)thiophene

Dicyclohexylcarbodiimide (0.4 g) is added to a solution of 2-hydroxy-5-(4'-hexylbiphenyl-4-yl)thiophene (0.25 g), (E)-hex-2-enoic acid, (0.2 g) 4-(dimethylamino)pyridine (0.10 g) and dichloromethane (50 cm$^3$) at 0° C. under an atmosphere of nitrogen. The reaction mixture is stirred overnight at room temperature, filtered to remove inorganic material and the filtrate evaporated down. The residue is purified by column chromatography on silica gel using hexanelethyl acetate (9/1 v/v) as eluent and recrystallisation from hexane to yield 0.16 g of 2-[(E)-hex-2-enoyloxy]-5-(4'-hexylbiphenyl-4-yl)thiophene.

The 2-hydroxy-5-(4'-hexylbiphenyl-4-yl)thiophene required as starting material could be prepared as follows:

A 1M solution of boron tribromide in dichloromethane (50 cm$^3$) is added dropwise to a solution of 2-propyloxy-5-(4'-hexylbiphenyl-4-yl)thiophene [Zh. Org. Khim., (1979) Vol. 49, pp. 476] (1.0 g) and dichloromethane (50 cm$^3$) at 0° C. under an atmosphere of nitrogen. The reaction solution is stirred overnight and water (100 cm$^3$) added. The organic layer is separated off and the aqueous layer extracted with dichloromethane (2×100 cm$^3$). The combined organic layers are washed with brine (2×100 cm$^3$) and then dried (MgSO$_4$), filtered and evaporated down. The residue is purified by column chromatography on silica gel using a 9:1 hexane/ethyl acetate mixture as eluent and recrystallisation from ethanol to yield 0.4 g of g 2-hydroxy-5-(4'-hexylbiphenyl-4-yl)thiophene.

The following compounds could be obtained analogously:
2-[(E)-But-2-enoyloxy]-5-(4'-propylbiphenyl-4-yl)thiophene.
2-[(E)-Pent-2-enoyloxy]-5-(4'-propylbiphenyl-4-yl)thiophene.
2-[(E)-Hex-2-enoyloxy]-5-(4'-propylbiphenyl-4-yl)thiophene.
2-[(E)-Hept-2-enoyloxy]-5-(4'-propylbiphenyl-4-yl)thiophene.
2-[(E)-Oct-2-enoyloxy]-5-(4'-propylbiphenyl-4-yl)thiophene.
2-[(E)-But-2-enoyloxy]-5-(4'-pentylbiphenyl-4-yl)thiophene.
2-[(E)-Pent-2-enoyloxy]-5-(4'-pentylbiphenyl-4-yl)thiophene.
2-[(E)-Hex-2-enoyloxy]-5-(4'-pentylbiphenyl-4-yl)thiophene.
2-[(E)-Hept-2-enoyloxy]-5-(4'-pentylbiphenyl-4-yl)thiophene.
2-[(E)-Oct-2-enoyloxy]-5-(4'-pentylbiphenyl-4-yl)thiophene.

EXAMPLE 12

Preparation of 2-[(E)-hex-2-Enyloxy]-5-(4'-hexylbiphenyl-4-yl)thiophene

Triphenylphosphine (1.4 g) is added in small portions to a solution of (E)-hex-2-en-1-ol (0.60 g), 2-hydroxy-5-(4'-hexylbiphenyl-4-yl)thiophene (0.50 g), diethylazodicarboxylate (0.80 g) in dry tetrahydrofuran (100 cm$^3$) at 0° C. under an atmosphere of nitrogen. The reaction mixture is stirred at room temperature overnight. The solvent is removed under reduced pressure and the crude product was purified by column chromatography on silica gel using a 4:1 petroleum (40–60° C.) ether/ethyl acetate mixture as eluent, followed by recrystallisation from ethanol to yield 0.12 g of 2-[(E)-hex-2-enyloxy]-5-(4'-hexylbiphenyl-4-yl)thiophene.

The following compounds could be obtained analogously:
2-[(E)-But-2-enyloxy]-5-(4'-propylbiphenyl-4-yl)thiophene.

2-[(E)-Pent-2-enyloxy]-5-(4'-propylbiphenyl-4-yl)thiophene.

2-[(E)-Hex-2-enyloxy]-5-(4'-propylbiphenyl-4-yl)thiophene.

2-[(E)-Hept-2-enyloxy]-5-(4'-propylbiphenyl-4-yl)thiophene.

2-[(E)-Oct-2-enyloxy]-5-(4'-propylbiphenyl-4-yl)thiophene.

2-[(E)-But-2-enyloxy]-5-(4'-pentylbiphenyl-4-yl)thiophene.

2-[(E)-Pent-2-enyloxy]-5-(4'-pentylbiphenyl-4-yl)thiophene.

2-[(E)-Hex-2-enyloxy]-5-(4'-pentylbiphenyl-4-yl)thiophene.

2-[(E)-Hept-2-enyloxy]-5-(4'-pentylbiphenyl-4-yl)thiophene.

2-[(E)-Oct-2-enyloxy]-5-(4'-pentylbiphenyl-4-yl)thiophene.

EXAMPLE 13

Preparation of 1-(4-[(E)-hex-2-Enyloxy]phenyl)-2-(2-cyanothiophen-5-yl)acetylene A solution of N,N-dicyclohexylcarbodiimide (0.22 g) in dichloromethane (10 cm$^3$) is added to a solution of (E)-hex-2-enoic acid (0.10 g), 1-(4-hydroxyphenyl)-2-(2-cyanothiophen-5-yl)acetylene (0.32 g), 4-(dimethylamino)pyridine (0.04 g) in dichloromethane (20 cm$^3$), cooled in an ice bath (0° C.) under an atmosphere of nitrogen. The reaction mixture is stirred overnight, filtered to remove precipitated material and the filtrate is evaporated down under reduced pressure. The crude product is purified by column chromatography on silica gel using a 9:1 petroleum ether (40–60° C.)/ethyl acetate mixture as eluent, followed by recrystallisation from ethanol to yield 1-(4-[(E)-hex-2-enyloxy]phenyl)-2-(2-cyanothiophen-5-yl)acetylene (0.26 g).

The 1-(4-hydroxyphenyl)-2-(2-cyanothiophen-5-yl)acetylene required as starting material could be prepared as follows:

A mixture of sodium ethoxide (0.7 g), 1-(4-methoxyphenyl)acetylene (0.5 g), and toluene (40 cm$^3$) is stirred for 2 h, 2-bromo-5-cyanothiophene (0.7 g), is added and the resultant mixture heated under reflux for 3 h. The reaction mixture is poured into water (500 cm$^3$) and the organic layer separated off. The aqueous layer is then extracted with toluene (2×50 cm$^3$). The combined organic layers are washed with water (2×200 cm$^3$), dried (MgSO$_4$), filtered and then evaporated down. The residue is purified by column chromatography on silica gel using a 95:5 hexane/ethyl acetate mixture as eluent and recrystallisation from ethanol to yield 0.3 g of 1-(4-methoxyphenyl)-2-(2-cyanothiophen-5-yl)acetylene.

A 1M solution of boron tribromide in dichloromethane (75 cm$^3$) is added dropwise to a solution of 1-(4-methoxyphenyl)-2-(2-cyanothiophen-5-yl)acetylene (3.0 g) and dichloromethane (100 cm$^3$) at 0° C. under an atmosphere of nitrogen. The reaction solution is stirred overnight and water (100 cm$^3$) added. The organic layer is separated off and the aqueous layer extracted with dichloromethane (2×100 cm$^3$). The combined organic layers are washed with brine (2×100 cm$^3$) and then dried (MgSO$_4$), filtered and evaporated down. The residue is purified by column chromatography on silica gel using a 9:1 hexane/ethyi acetate mixture as eluent and recrystallisation from ethanol to yield 1.8 g of g 1-(4-hydroxyphenyl)-2-(2-cyanothiophen-5-yl)acetylene.

The following compounds could be obtained analogously:

1-(4-[(E)-But-2-enyloxy]phenyl)-2-(2-cyanothiophen-5-yl)acetylene.

1-(4-[(E)-Pent-2-enyloxy]phenyl)-2-(2-cyanothiophen-5-yl)acetylene.

1-(4-[(E)-Hept-2-enyloxy]phenyl)-2-(2-cyanothiophen-5-yl)acetylene.

1-(4-[(E)-Oct-2-enyloxy]phenyl)-2-(2-cyanothiophen-5-yl)acetylene.

Some of the compounds described by the current invention were investigated in the host mixture DOP-017 which is a mixture of alkylcyclohexyl-COO-phenylOR and alkyl-cyclohexylphenylCN.

The compounds were individually doped 10% into the host and the clearing points determined. The structure of the compounds and the phase behaviour of the mixtures is detailed in Table 1.

TABLE 1

| Mixture | Compound Identity | Structure | Transition Temperatures of the mixtures (° C.) |
|---------|-------------------|-----------|------------------------------------------------|
| AGB143  | WD266             |           | Iso-53.4-N                                     |
| AGB144  | WD267             |           | Iso-51.8-N                                     |
| AGB145  | WD272             |           | Iso-51.4-N                                     |

TABLE 1-continued

| Mixture | Compound Identity | Structure | Transition Temperatures of the mixtures (° C.) |
|---|---|---|---|
| AGB146 | WD268 | $C_5H_{11}$—thiophene—phenyl—O—C(=O)—CH=CH—C_3H_7 | Iso-51.6-N |
| AGB147 | WD269 | $C_5H_{11}$—thiophene—phenyl—O—C(=O)—CH=CH—C_4H_9 | Iso-51.3-N |

The burefringence and refractive indices of the mixtures were determined and the results are shown in Table 2 with DOP-017 for comparison.

TABLE 2

| Mixture | Temperature (° C.) | $n_o$ | $n_e$ | n | Δn |
|---|---|---|---|---|---|
| AGB143 | 50 | 1.4891 | 1.5516 | 1.5308 | 0.0625 |
|  | 45 | 1.4872 | 1.5667 | 1.5402 | 0.0794 |
|  | 40 | 1.4874 | 1.5724 | 1.5441 | 0.0850 |
|  | 35 | 1.4877 | 1.5793 | 1.5488 | 0.0915 |
|  | 30 | 1.4858 | 1.5843 | 1.5522 | 0.0963 |
|  | 25 | 1.4885 | 1.5890 | 1.5555 | 0.1005 |
| AGB144 | 50 | 1.4890 | 1.5578 | 1.5349 | 0.0688 |
|  | 45 | 1.4877 | 1.5654 | 1.5395 | 0.0778 |
|  | 40 | 1.4881 | 1.5737 | 1.5452 | 0.0855 |
|  | 35 | 1.4885 | 1.5784 | 1.5484 | 0.0899 |
|  | 30 | 1.4890 | 1.5837 | 1.5521 | 0.0947 |
|  | 25 | 1.4818 | 1.5882 | 1.5552 | 0.0991 |
| AGB145 | 50 | 1.4888 | 1.5564 | 1.5339 | 0.0676 |
|  | 45 | 1.4875 | 1.5662 | 1.5399 | 0.0786 |
|  | 40 | 1.4877 | 1.5726 | 1.5443 | 0.0850 |
|  | 35 | 1.4877 | 1.5764 | 1.5469 | 0.0887 |
|  | 30 | 1.4882 | 1.5827 | 1.5512 | 0.0946 |
|  | 25 | 1.4887 | 1.5876 | 1.5546 | 0.0989 |
| AGB146 | 50 | 1.4879 | 1.5560 | 1.5333 | 0.0681 |
|  | 45 | 1.4867 | 1.5537 | 1.5391 | 0.0787 |
|  | 40 | 1.4868 | 1.5735 | 1.5447 | 0.0868 |
|  | 35 | 1.4871 | 1.5793 | 1.5486 | 0.0922 |
|  | 30 | 1.4875 | 1.5836 | 1.5516 | 0.0960 |
|  | 25 | 1.4881 | 1.5865 | 1.5537 | 0.0984 |
| AGB147 | 50 | 1.4885 | 1.5564 | 1.5346 | 0.0691 |
|  | 45 | 1.4873 | 1.5666 | 1.5402 | 0.0793 |
|  | 40 | 1.4871 | 1.5714 | 1.5432 | 0.0843 |
|  | 35 | 1.4873 | 1.5771 | 1.5471 | 0.0898 |
|  | 30 | 1.4881 | 1.5831 | 1.5514 | 0.0950 |
|  | 25 | 1.4885 | 1.5880 | 1.5549 | 0.0995 |
| DOP-017 | 40 | 1.4834 | 1.5658 | 1.5109 | 0.0825 |
|  | 25 | 1.4854 | 1.5796 | 1.5168 | 0.0943 |
|  | 20.6 | 1.4862 | 1.5832 | 1.5185 | 0.0970 |
|  | 0 | 1.4904 | 1.5977 | 1.5261 | 0.1074 |

One known device in which the materials of the current invention may be incorporated is the twisted nematic (TN) device which uses a thin layer of a nematic material between glass slides. The slides are unidirectionally rubbed and assembled with the rubbing directions orthogonal. The rubbing gives a surface alignment to the liquid crystal molecules resulting in a progressive 90° twist across the layer. When placed between polarisers, with their optical axis perpendicular or parallel to a rubbing direction the device rotates the plane of polarised light in its OFF state and transmits without rotation in the ON state. Small amounts of chiral material which may or may not be cholesteric may be added to the nematic material to ensure the 90° twist is of the same sense across the whole area of the device as explained in UK patents 1,472,247 and 1,478,592.

An improvement in the performance of large, complex, nematic LCDs occurred in 1982 when it was observed that the voltage dependence of the transmission of nematic LC layers with twist angles in the range 180° to 270° could become infinitely steep, see C. M. Waters, V. Brimmell and E. P. Raynes, Proc. 3rd Int. Display Res. Conf., Kobe, Japan, 1983, 396. The larger twist angles are produced by a combination of surface alignment and making the nematic mixture into a long pitch cholesteric by the addition of a small amount of a chiral twisting agent. The increasing twist angle steepens the transmission/voltage curve, until it becomes bistable for 270° twist; for a specific twist angle between 225° and 270° the curve becomes infinitely steep and well suited to multiplexing. The larger twist angles present have resulted in the name supertwisted nematic (STN) for these LCDs. The materials of the present invention may also be used in such devices.

Liquid Crystal Devices describing the use of STNs may be found in patent application GB 8218821 and resulting granted patents including U.S. Pat. No. 4,596,446.

SID M6/1–37 volume 1 seminar lecture notes, May 1998 describes both active and passive STNs in which the materials of the current invention may be incorporated.

Two types of device are commonly known as passive matrix and active matrix liquid crystal devices.

Figure 1:
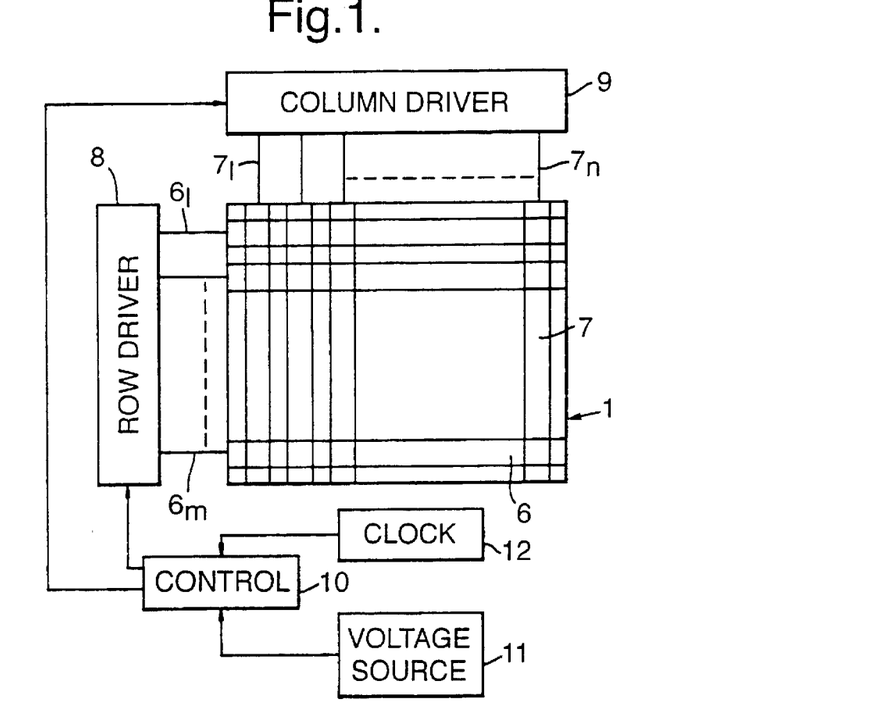
FIG. 1 is a plan view of a matrix multiplex addressed liquid crystal display.
Figure 2:
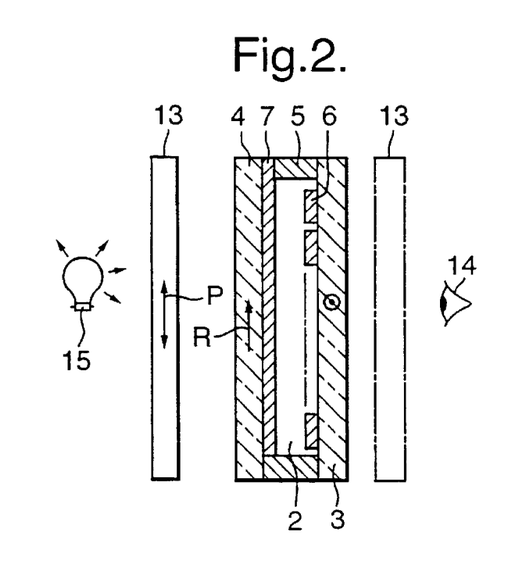
FIG. 2 is a cross-section of a display such as FIG. 1 used in a transmissive mode.

The display of FIGS. 1 and 2 comprises a liquid crystal cell 1 formed by a layer 2 of nematic or cholesteric liquid crystal material contained between glass walls 3,4. A spacer ring 5 maintains the walls typically 6 μm apart. For passive matrix devices strip like row electrodes $6_1$ to $6_m$, e.g. of $SnO_2$ are formed on one wall 3 and similar column electrodes $7_1$ to $7_n$ formed on the other wall 4. With m-row electrodes and n-column electrodes this forms an mxn matrix of addressable elements. Each element. is formed by the interaction of a row and column electrode. For active matrix devices a discrete nonlinear device eg a transistor or diode is associated with each pixel.

For the passive matrix device a row driver supplies voltage to each row electrode 6. Similarly a column drive 9 supplies voltages to each column electrode 7. Control of applied voltages is from a control logic 10 which receives power from a voltage source 11 and timing from a clock 12.

For an active device e.g., a thin film transistor active matrix liquid crystal device (TFT AMLCD) three types of electrodes are present, pixel, scanning and signal electrodes as well as a common electrode on the opposite side of the liquid crystal. The control electrode operates the gate such that the voltage on the signal electrode is applied to the relevant pixel electrode.

An example of the use of a material and device embodying the present invention will now be described with reference to FIG. 2.

The liquid crystal device consists of two transparent plates, 3 and 4, for example made from glass, in the case of an active matrix device these will usually be ofaluminosilicate (alkali free) glass often with a passivation layer of $SiO_2$. For an active matrix display the active deviceseg thin film transistors, are fabricated and a colour filter layer is added for a full colour display. These plates are coated on their internal face with transparent conducting electrodes 6 and 7, often ITO which is patterned using photolithography techniques. An alignmentlayer is introduced onto the internal faces of the cell so that a planar orientation of the molecules making up the liquid crystalline material will be approximately parallel to the glass plates 3 and 4. This is done by coating the glass plates 3,4 complete with conducting electrodes; the intersections between each column and row electrode form an x, y matrix of addressable elements or pixels. For some types of display the alignment directions are orthogonal. Prior to the construction of the cell the alignment layers are rubbed with a roller covered in cloth (for example made from velvet) in a given direction, the rubbing directions being arranged parallel (same or opposite direction) upon construction of the cell. A spacer 5 e.g. ofpolymethyl methacrylate separates the glass plates 3 and 4 to a suitable distance e.g. 2–7 microns preferably 4–6 microns. Liquid crystal material 2 is introduced between glass plates 3,4 by filling the space in between them. This may be done by flow filling the cell using standard techniques. The spacer 5 is sealed with an adhesive in a vacuum using an existing technique. Polarisers 13 may be arranged in front of and behind the cell.

Alignment layers may be introduced onto one or more of the cell walls by one or more of the standard surface treatment techniques such as rubbing, oblique evaporation or as described above by the use of polymer aligning layers.

In alternative embodiments the substrates with the aligning layers on them are heated and sheared to induce alignment, alternatively the substrates with the aligning layers are thermally annealed above the glass transition temperature and below the liquid crystal to isotropic phase transition in combination with an applied field. Further embodiments may involve a combination of these aligning techniques. With some of these combinations an alignment layer may not be necessary. It is also possible to use so-called non-contact alignment layers in both passive and active devices described by the current invention.

Figure 3:
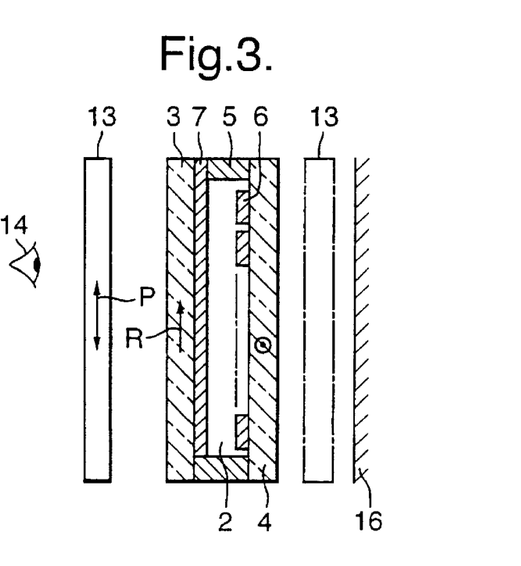
FIG. 3 is similar to FIG. 2 but operates in a reflective mode.

The device may operate in a transmissive or reflective mode. In the former, light passing through the device, e.g. from a tungsten bulb, is selectively transmitted or blocked to form the desired display. In the reflective mode a mirror, or diffuse reflector, (16) is placed behind the second polariser 13 to reflect ambient light back through the cell and twopolarisers. By making the mirror partly reflecting the device may be operated both in atransmissive and reflective mode.

The alignment layers have two functions, one to align contacting liquid crystal molecules in a preferred direction and the other to give a tilt to these molecules—a so called surface tilt—of a few degrees typically around 4° or 5°. The alignment layers may be formed by placing a few drops of the polyimide on to the cell wall and spinning the wall until a uniform thickness is obtained. The polyimide is then cured by heating to a predetermined temperature for a predetermined time followed by unidirectional rubbing with a roller coated with a nylon cloth. In an alternative embodiment a single polariser and dye material may be combined. The materials of the current invention may also be used in LCDs with an actively addressed matrix e.g. thin film transistors (TFT-LCDs) or a passively addressed matrix e.g., dual scan STN. SID M3/1–52 volume 1 seminar lecture notes, May 1998 describes a typical AMLCD in which the materials of the current invention may be incorporated. The materials of the present invention may be used in those devices which utilise the flexoelectric effect for example in bistable devices using nematic liquid crystal materials as described in PCT/GB96/02463 the contents of which are hereby incorporated by reference. For use in the devices described in PCT/GB96102463 the materials of the present are of particular use due to inter alia one or more of the following characteristics—fast switching times, low switching voltage which is due mainly to a large flexoelectric coefficient and a low viscosity. Similarly the materials of the present invention may also be used in the bistable devices described and claimed in PCT/GB95/00179 the contents of which are hereby incorporated by reference.

For a bistable nematic device, with reference to FIGS. 1–3—either side of the cell 1 are polarisers 13 arranged with their polarisation axes substantially crossed with respect to one another and at an angle of substantially 45° to an alignment direction, if any, on the adjacent wall 3, 4. Additionally an optical compensation layer (not shown) of e.g. stretched polymer may be added adjacent to the liquid crystal layer 2 between cell wall and polariser.

A partly reflecting mirror 16 may be arranged behind the cell 1 (as shown in FIG. 3) together with a light source behind the mirror (not shown). These allow the display to be seen in reflection and lit from behind in dull ambient lighting. For a transmission device, the mirror 16 may be omitted.

Prior to assembly, at least one of the cell walls 3, 4 are treated with alignment gratings to provide a bistable pretilt. The other surface may be treated with either a planar (i.e. zero or a few degrees of pretilt with an alignment direction) or homeotropic monostable surface, or a degenerate planar surface (i.e. a zero or few degrees of pretilt with no alignment direction). Finally the cell is filled with a mixture comprising a material as described in the current application. Fabrication of the grating surfaces is described in PCTIGB96/02463 and references therein.

What is claimed is:

1. A compound of Formula 1:

Formula I wherein

RJ is $C_nH_{2n+1}CH=CHC_mH_{2m}Z_1$ n is 1–5;

m is 0–5;

q is 0, 1 or 2;

$A_1$, $A_2$ are independently chosen from 2,5-disubstituted furan, 2,5-disubstituted thiophene, 2,5-disubstituted oxazole, 2,5-disubstituted thiazole, 2,5-disubstituted 1,3,4-oxadiazole, 2,5-disubstituted 1,3,4-thiadiazole, 1,4-disubstituted benzene, 2,5-disubstituted pyrimidine, 2,5-disubstituted pyridine, 2,6-disubstituted naphthalene;

laterally substituted 1,4-disubstituted benzene, laterally substituted 2,5-disubstituted pyrimidine, laterally substituted 2,5-disubstituted pyridine, laterally substituted 2,6-disubstituted naphthalene wherein the lateral substituents are independently selected from F, Cl, Br or CN and present in any of the available substitution positions;

$A_3$ is 2,5-disubstituted furan, 2,5-disubstituted thiophene, 2,5-disubstituted oxazole, 2,5-disubstituted thiazole, 2,5-disubstituted 1,3,4-oxadiazole, 2,5-disubstituted 1,3,4-thiadiazole, 1,4-disubstituted benzene, 2,5-disubstituted pyrimidine, 2,5-disubstituted pyridine, 2,6-disubstituted naphthalene; laterally substituted 1,4-disubstituted benzene, laterally substituted 2,5-disubstituted pyrirnidine, laterally substituted 2,5-disubstituted pyridine laterally substituted 2,6-disubstituted naphthalene wherein the lateral substituents are independently selected from F, Cl, Br or CN and is present in any of the available substitution positions; 1,4-disubstituted bicyclo(2.2.2)octane, trans-1,4-disubstituted cyclohexane, trans-2,5-disubstituted dioxane, or 1,4-disubstituted piperidine;

$Z_1$ is O, COO or OOC;

$Z_2$ and $Z_3$ are independently selected from a direct bond, COO, OOC, $C_2H_4$, $CH_2O$, $OCH_2$, $C_4H_8$, $C_3H_6O$, (E)-$CH=CHC_2H_4$, (Z)-$CH_2CH=CHCH_2$, (E)-$CH=CHCH_2O$ or —C≡C—;

R is alkyl, alkoxy, alkenyl, alkenyloxy, alkanoyloxy, alkenoyloxy or $OC_pF_{2p+1}$, and R contains 1 to 20 carbon atoms and is branched or a straight chain; and p is 1–20;

provided that:

when $Z_1$ is O and m is 1, 3 or 5 the carbon-carbon double bond configuration in RJ is E, and when

$Z_1$ is O and m is 2 or 4 the carbon-carbon double bond configuration in RJ is Z, and when $Z_1$ is COO or OOC and m is 0, 2 or 4 the carbon-carbon double bond configuration in RJ is E, and when $Z_1$ is COO or OOC and m is 1, 3 or 5 the carbon-carbon double bond configuration in RJ is Z;

wherein at least one of $A_1$ $A_2$ or $A_3$ comprises one of the 5-membered heterocyclic rings listed above.

2. A compound selected from the group consisting of:

wherein n is 1–5, m is 0–5 and q is 0 or 1 and when q is 0 then $A_3$ is aromatic;

$A_1$ and $A_2$ are 2,5-disubstituted furan, 2,5-disubstituted thiophene, 2,5-disubstituted oxazole, 2,5-disubstituted thiazole, 2,5-disubstituted 1,3,4-oxadiazole, 2,5-disubstituted 1,3,4-thiadiazole, or 1,4-disubstituted benzene;

$Z_1$ is O or COO;

$Z_2$ and $Z_3$ are direct bonds or —C≡C—;

R is alkyl, alkoxy, alkenyl or alkenyloxy and has one to seven carbon atoms;

wherein at least one of $A_1$ $A_2$ or $A_3$ comprises one of the 5-membered heterocyclic rings listed above.

3. A liquid crystal mixture comprising at least one compounds of claimed or claim 1 or claim 2.

4. A device comprising two spaced cell walls each bearing electrode structures and treated on at least one facing surface with an alignment layer, a layer of a liquid crystal material enclosed between the cell walls, wherein the liquid crystal material comprises a compound of claim 1 or 2.

5. A device comprising two spaced cell walls each bearing electrode structures and treated on at least one facing surface with an alignment layer, a layer of a liquid crystal mixture enclosed between the cell walls, the liquid crystal mixture incorporates the liquid crystal mixture of claim 3.

6. A liquid crystal device according to claim 4, wherein the device is an active matrix device, an STN device or a TN device.

7. A liquid crystal device according to claim 5, wherein the device is an active matrix device, an STN device, or a TN device.

8. A bistable nematic liquid crystal device comprising:

two cell walls enclosing a layer of liquid crystal material;

electrode structures on both cell walls;

a surface alignment on the facing surfaces of both cell walls providing alignment to liquid crystal molecules;

means for distinguishing between switched states of the liquid crystal material;

a surface alignment grating on at least one cell wall that permits the liquid crystal molecules to adopt two different pretilt angles in the same azimuthal plane;

the arrangement being such that two stable liquid crystal molecular configurations can exist after suitable electrical signals have been applied to the electrodes;

wherein the layer of liquid crystal material comprises a mixture as defined in claim 3.

9. The device of claim 8 wherein the grating comprises a single asymmetric modulation whose groove depth and pitch ratio provides bistable alignment.

10. The device of claim 8 wherein the grating comprises a single symmetric modulation whose groove depth and pitch ratio provides bistable alignment.

* * * * *